(12) United States Patent
Taneja

(10) Patent No.: US 11,634,744 B2
(45) Date of Patent: Apr. 25, 2023

(54) METHODS AND MATERIALS FOR ASSESSING AND TREATING ARTHRITIS

(71) Applicant: Mayo Foundation for Medical Education and Research, Rochester, MN (US)

(72) Inventor: Veena Taneja, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 750 days.

(21) Appl. No.: 16/582,042

(22) Filed: Sep. 25, 2019

(65) Prior Publication Data

US 2020/0087701 A1  Mar. 19, 2020

Related U.S. Application Data

(62) Division of application No. 15/547,107, filed as application No. PCT/US2016/016385 on Feb. 3, 2016, now Pat. No. 10,465,224.

(60) Provisional application No. 62/111,215, filed on Feb. 3, 2015.

(51) Int. Cl.
| | |
|---|---|
| *A61P 37/00* | (2006.01) |
| *C12Q 1/04* | (2006.01) |
| *G01N 33/68* | (2006.01) |
| *A61K 35/66* | (2015.01) |
| *A61K 35/741* | (2015.01) |
| *A61P 19/02* | (2006.01) |
| *C12Q 1/689* | (2018.01) |

(52) U.S. Cl.
CPC ............... *C12Q 1/04* (2013.01); *A61K 35/66* (2013.01); *A61K 35/741* (2013.01); *A61P 19/02* (2018.01); *A61P 37/00* (2018.01); *C12Q 1/689* (2013.01); *G01N 33/6806* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 5,965,787 A | 10/1999 | Luthra et al. | |
| 8,617,536 B2 | 12/2013 | Murray et al. | |
| 9,005,603 B2 | 4/2015 | Murray et al. | |
| 9,555,066 B2 | 1/2017 | Murray et al. | |
| 9,801,914 B2 | 10/2017 | Murray et al. | |
| 10,465,224 B2 | 11/2019 | Taneja et al. | |
| 10,555,975 B2 | 2/2020 | Murray et al. | |
| 2004/0126372 A1 | 7/2004 | Banerjee et al. | |
| 2004/0170617 A1 | 9/2004 | Finegold | |
| 2007/0154414 A1 | 7/2007 | Bonfiglio | |
| 2008/0241226 A1 | 10/2008 | Abeln et al. | |
| 2011/0047632 A1 | 2/2011 | Robinson et al. | |
| 2012/0213833 A1 | 8/2012 | Murray et al. | |
| 2013/0121968 A1 | 5/2013 | Quay | |
| 2014/0105972 A1 | 4/2014 | Murray et al. | |
| 2015/0290256 A1 | 10/2015 | Murray et al. | |
| 2017/0189455 A1 | 7/2017 | Murray et al. | |
| 2018/0010164 A1 | 1/2018 | Taneja | |
| 2018/0021390 A1 | 1/2018 | Murray et al. | |
| 2018/0249688 A1 | 9/2018 | Ayares et al. | |
| 2022/0031765 A1 | 2/2022 | Bellone et al. | |

FOREIGN PATENT DOCUMENTS

| | | |
|---|---|---|
| WO | WO 2011/140208 | 11/2011 |
| WO | WO 2012/163768 | 6/2012 |
| WO | WO 2013/036290 | 3/2013 |
| WO | WO 2014/110090 | 7/2014 |
| WO | WO 2014/137211 | 9/2014 |
| WO | WO 2014/159510 | 10/2014 |
| WO | WO 2019/051381 | 3/2019 |
| WO | WO 2020/109620 | 6/2020 |

OTHER PUBLICATIONS

Morita, S., et al. Resp. Case Rep.2(2):1-3 (Year: 2014).*
Kwon, H.K., et al. P.N.A.S.107(5):2159-2164 (Year: 2010).*
Fiset, P.E. Can. Med. Assoc. J. ;47(6):545-547 (Year: 1942).*
Khan, M. T., et al. Plos ONE;9(5):1-7 (Year: 2014).*
Alauzet et al., "*Prevotella nanceiensis* sp. nov., isolated from human clinical samples," International J Systematic Evol Microbiol., 27:2216-2220, 2007.
Arumugam et al., "Enterotypes of the human gut microbiome," Nature., 473(7346):174-180, May 12, 2011.
Bedaiwi and Inman., "Microbiome and probiotics: link to arthritis," Curr Opin Rheumatol., 26(4):410-415, Jul. 2014.
Bellance et al., "Oncosecretomics coupled to bioenergetics identifies α-amino adipic acid, isoleucine and GABA as potential biomarkers of cancer: Differential expression of c-Myc, Oct1 and KLF4 coordinates metabolic changes," Biochimica et Biophysica Acta, 1817:2060-2071, Nov. 2012.
Bradley et al., "HLA-DQB1 polymorphism determines incidence, onset, and severity of collagen-induced arthritis in transgenic mice. Implications in human rheumatoid arthritis," J Clin. Invest., 100:2227-2234, 1997.
"Breedveld and Day er., ""Leflunomide: mode of action in the treatment of Rheumatoid arthritis,"" Ann Rheum Dis., 59(11):841-849, Nov. 2000".
Brehm et al., "Advancing animal models of human type 1 diabetes by engraftment of functional human tissues in immunodeficient mice," Cold Spring Harb Perpect Med., 2(5):1-13, May 2012.
Carvalho et al., "Survival of freeze-dried lactobacillus plantarum and lactobacillus rhamnosus during storage in the presence of protectants," Biotechnology Lett., 24:1587-1591, 2002.

(Continued)

*Primary Examiner* — G. R. Ewoldt
(74) *Attorney, Agent, or Firm* — Fish & Richardson P.C.

(57) ABSTRACT

This document provides methods and materials involved in assessing mammals (e.g., humans) for arthritis. For example, methods and materials for assessing a mammal's gut microbial diversity to identify the mammal as having arthritis (e.g., rheumatoid arthritis) are provided. This document also provides methods and materials involved in treating arthritis.

2 Claims, 25 Drawing Sheets

Specification includes a Sequence Listing.

(56) References Cited

OTHER PUBLICATIONS

Chervonsky., "Influence of microbial environment on autoimmunity," Nature Immunol., 11(1):28-35, Jan. 2010.
Crenn et al., "Citrulline as a biomarker of intestinal failure due to enterocyte mass reduction," ClinNutr., 27(3):328-339, Jun. 2008.
Das et al., "Complementation between specific HLA-DR and HLA-DQ genes in transgenic mice determines susceptibility to experimental autoimmune encephalomyelitis," Hum Immunol., 61(3):279-289, Mar. 2000.
Ding and Schloss., "Dynamics and associations of microbial community types across the human body," Nature., 509(7500):357-360, May 15, 2014.
Downes et al., "*Prevotella histicola* sp. nov., isolated for the human oral cavity," International J. Systematic Evol. Microbiol., 58:1788-1791, 2008.
Ebringer et al., "Rheumatoid arthritis, proteus, anti-CCP antibodies and Karl Popper," Autoimmun Rev., 9(4):216-223, Feb. 2010.
Eerola et al., "Intestinal flora in early rheumatoid arthritis," Brit J Rheumatol., 33:1030-1038, 1994.
Filteau, "[Chromatography of the amino acids of the serum]," Laval Med., 27(4):465-475, Apr. 1959.
Gomez et al., "Loss of sex and age driven differences in the gut microbiome characterize arthritis-susceptible 0401 mice but not arthritis-resistant 0402 mice," PLOS One., 7(4):e36095, 2012, 11 pages.
Greenblum et al., "Metagenomic systems biology of the human gut microbiome reveals topological shifts associated with obesity and inflammatory bowel disease," PNAS., 109(2):594-599, Jan. 10, 2012.
Griffiths et al., "Immunogenetic control of experimental type II collagen-induced arthritis. I. Susceptibility and resistance among inbred strains of rats," Arthritis Rheum., 24(6):781-789, Jun. 1981.
Hajati et al., J Oral Maxillofac Surg. Sep. 2009; 67(9): 1895-1903.
Hatakka et al., "Effects of pro biotic therapy on the activity and activation of mild rheumatoid arthritis—a pilot study," Scand J Rheumatol., 32(4):211-215, 2003.
Jackson et al., "The effect of the commensal bacterium, Prevotella nanceiensis, on experimental autoimmune encephalomyelitis, an animal model for multiple sclerosis," Kentucky Acad of Sci Annual Meeting, 2008, 30 pages.
Jiang et al., "Salivary microbiome diversity in caries-free and caries-affected children," Int J Mol Sci., 17(1978):1-13, 2016.
Kamada et al., "Role of the gut microbiota in immunity and inflammatory disease," Nat Rev Immun., 13(5):321-335, May 1, 2013.
Kaur et al., "Probiotics: delineation of prophylactic and therapeutic benefits," J Medicinal Food., 12(2):219-235, 2009.
Klareskog et al., "Mechanisms of disease: Genetic susceptibility and environmental triggers in the development of rheumatoid arthritis," Nat Clin Pract Rheumatol., 2(8):425-433, Aug. 2006.
Lampson et al., "Two populations of Ia-like molecules on a human B cell line," J Immunol., 125:293-299, 1980.
Lanza et al., "Quantitative Metabolomics by 1H-NMR and LC-MS/MS Confirms Altered Metabolic Pathways in Diabetes," PLoS One, 5(5): 10538, Ma 2010.
Luckey et al., "Bugs & us:the role of the gut in autoimmunity," Indian J Med Res., 138(5):732-743, Nov. 2013.
Mangalam et al., "HLA-DQ8 (DQB1*0302)-Restricted Th17 Cells Exacerbate Experimental Autoimmune Encephalomyelitis in HLA-DR3-Transgenic Mice," J Immunol., 182(8):5131-5139, 2009.
Marques et al., "Septic arthritis of the knee due to Prevotella loescheii following tooth extraction," Med Oral Pathol Oral Cir Bucal., 13(8):E505-E507, 2008.
Mielcarz et al., "FTY720 Ameliorates Pathogen Driven Ileitis in C57BL/6 Mice by Impeding Lymphocyte Trafficking," Clin Immunol., 127:S122, Jan. 2008.
Morgan et al., "Dysfunction of the intestinal microbiome in inflammatory bowel disease and treatment," Genome Biol., 13(9):R79, Apr. 16, 2012.

Moritani et al., "Acetaldehyde production by major oral microbes," Oral Dis., 21(6):748-754, Sep. 2015, Abstract.
Nenonen et al., "Uncooked, lactobacilli-rich, vegan food and rheumatoid arthritis," Br J Rheumatol., 37(3):274-281, Mar. 1998.
Nielen et al., "Specific autoantibodies precede the symptoms of rheumatoid arthritis: a study of serial measurements in blood donors," Arthritis Rheum., 50(2):380-386, Feb. 2004.
Nouailles et al., "CXCL5-secreting pulmonary epithelial cells drive destructive neutrophilic inflammation in tuberculosis," J Clin Invest., 124(3):1268-1282, Mar. 3, 2014.
Sampedro et al., "Species of Propionibacterium and Propionibacterium acnes phylotypes associated with orthopedic implants," Diagnostic Microbiol Infect. Dis., 64:138-145, 2009.
Scher et al., "Expansion of intestinal Prevotella copri correlates with enhanced susceptibility to arthritis," eLife., 2:e01202, 2013, 20 pages.
Severijnen et al., "Chronic arthritis induced in rats by cell wall fragments of *Eubacterium* species from the human intestinal flora," Infect Immun., 58(2):523-528, Feb. 1990.
Straub et al., "Negative and positive selection by HLA-DR3(DRw17) molecules in transgenic mice," Immunogenetics., 40(2):104-108, 1994.
Taneja and David., "HLA class II transgenic mice as models of human diseases," Immunol Rev., 169:67-79, Jun. 1999.
Taneja et al., "New humanized HLA-DR4-transgenic mice that mimic the sex bias of rheumatoid arthritis," Arthritis Rheum,, 56:69-78, Jan. 2007.
Taneja et al., "Delineating the Role of the HLA-DR4 "Shared Epitope" in Susceptibility versus Resistance to Develop Arthritis," J Immunol., 181:2869-2877, 2008.
Taneja., "Arthritis susceptibility and the gut microbiome," FEBS Lett., 588(22):4244-4249, Nov. 17, 2014.
Taneja., "The gut commensals for treating rheumatoid arthritis," Presented at the Microbiome and Autoimmune Disease Colloquium organized by The American Autoimmune related Disease Association., May 18, 2014, National Conference Center, 18980, Upper Belmont Place, Leesburg, VA., 28 pages.
Trang et al., Scand JRheumatol. 1985;14(4):393-402.
Turnbaugh et al., "A core gut microbiome in obese and lean twins," Nature., 457(7228):480-484, Jan. 22, 2009.
Turnbaugh et al., "The human microbiome project: exploring the microbial part of ourselves in a changing world," Nature., 449(7164):804-810, Oct. 18, 2007.
Vaahtovuo et al., "Fecal Microbiota in Early Rheumatoid Arthritis," J Rheumatol., 35(8):1500-15005, 2008.
Vaghef-Mehrabany et al., "Probiotic supplementation improves inflammatory status in patients with rheumatoid arthritis," Nutrition., 30(4):430-435, Apr. 2014.
Wikipedia document entitled 'Saliva', May 30, 2018, 7 pages.
Wooley, "Type II collagen-induced arthritis in mice. I. Major histocompatibility complex (I region) linkage and antibody correlates," J Exp. Med., 154:688-700, 1981.
Wu et al., "Gut-residing segmented filamentous bacteria drive autoimmune arthritis via T helper 17 cells," Immunity., 32(6):815-827, Jun. 25, 2010.
Yang et al., "T helper 17 lineage differentiation is programmed by orphan nuclear receptors RORα and RORγ," Immunity., 28(1):29-39, Jan. 2008.
Zhang et al., "What determines arthritogenicity of bacterial cell wall? A study on Eubacterium cell wallinduced arthritis," Rheumatol., 39:274-282, 2000.
Barnes, "Inflammatory mechanisms in patients with chronic obstructive pulmonary disease," J. Allergy Clin. Immunology, Jul. 2016, 138(1):16-27.
Barton et al., "Sa. 128. Simultaneous Oral Gluten and Microbial Exposure Increases Systemic Cytokine Suppression in a MHC Class II Dependent Manner," Clin. Immunology, Jun. 2008, 127(S):S122.
Bassis et al., "Analysis of the upper respiratory tract microbiotas as the source of the lung and gastric microbiotas in healthy individuals," mBio, Mar./Apr. 2015, 6(2):e00037-15, 10 pages.
Bradley et al., "Segmented Filamentous Bacteria Provoke Lung Autoimmunity by Inducing Gut-Lung Axis Th17 Cells Expressing Dual TCRs," Cell Host Microbe, Nov. 8, 2017, 22(5):697-704.e4.

(56) References Cited

OTHER PUBLICATIONS

Chen et al., "An expansion of rare lineage intestinal microbes characterizes rheumatoid arthritis," Genome Medicine, Apr. 21, 2016, 8(1):43, 14 pages.

Dethlefsen et al., "An ecological and evolutionary perspective on human-microbe mutualism and disease," Nature, Oct. 18, 2007, 449(7164):811-818.

Ewart et al., "Respiratory system mechanics in mice measured by end-inflation occlusion," J. Appl. Physiology, Aug. 1995, 79(2):560-566.

Hasleton, "The internal surface area of the lung in emphysema," Pathol. Eur., 1976, 11(3):211-218.

Jarvik et al., "Nicotine blood levels and subjective craving for cigarettes," Pharmacol. Biochem. Behavior, Jul. 2000, 66(3):553-558.

Jeraldo et al., "IM-TORNADO: A Tool for Comparison of 16S Reads from Paired-End Libraries," PLoS One, Dec. 15, 2014, 9(12):e114804, 19 pages.

Jumpstart Consortium Human Microbiome Project Data Generation Working Group, "Evaluation of 16S rDNA-Based Community Profiling for Human Microbiome Research," PLoS One, Jun. 13, 2012, 7(6):e39315, 14 pages.

Kroening et al., "Cigarette smoke-induced oxidative stress suppresses generation of dendritic cell IL-12 and IL-23 through ERK-dependent pathwaysm" J. Immunology, Jul. 15, 2008, 181(2):1536-1547.

Kudva et al., "Glycemic variation and hypoglycemia in patients with well-controlled type 1 diabetes on a multiple daily insulin injection program with use of glargine and ultralente as basal insulin," Endocr. Practice, May 2007, 13(3):244-250.

Kurimoto et al. "IL-17A is Essential to the Development of Elastase-Induced Pulmonary Inflammation and Emphysema in Mice," Respir. Research, Jan. 20, 2013, 14(1):5, 10 pages.

Kurup et al., "A cholesterol and actinide dependent shadow biosphere of archaea and viroids in autoimmune diseases," Immunobiology, Mar. 2012, 217(3):316-320.

Larsen, "The immune response to Prevotella bacteria in chronic inflammatory disease," J. Immunology, Aug. 2017, 151(4):363-374.

Mahmud et al., "Celiac Disease in Type 1 Diabetes Mellitus in a North American Community: Prevalence, Serologic Screening, and Clinical Features," Mayo Clin. Proceedings, Nov. 2005, 80(11):1429-1434.

Marietta et al., "A new model for dermatitis herpetiformis that uses HLA-DQ8 trangenic NOD mice," J. Clin. Investigation, Oct. 2004, 114(8):1090-1097.

Marietta et al., "Suppression of Inflammatory Arthritis by Human Gut-Derived Prevotella histicola in Humanized Mice," Arthritis Rheumatology, Dec. 2016, 68(12):2878-2888.

Marietta et al., "Transglutaminase Autoantibodies in Dermatitis Herpetiformis and Celiac Sprue, J. Inv. Dermatology," Feb. 2008, 128(2):332-335.

Ouyang et al., "IH NMR-based metabolomic study of metabolic profiling for systemic lupus erythematosus," Lupus, Nov. 2011, 20(13):1411-1420.

Piters et al., "Dysbiosis of upper respiratory tract micro biota in elderly pneumonia patients," ISME Journal, Jan. 2016, 10(1):97-108.

Rajagopalan et al., "Distinct local immunogenic stimuli dictate differential requirements for CD4+ and CD8+ T cell subsets in the pathogenesis of spontaneous autoimmune diabetes," Autoimmunity, Nov. 2007, 40(7):489-496.

Saetta et al., "Increased expression of the chemokine receptor CXCR3 and its ligand CXCL10 in peripheral airways of smokers with chronic obstructive pulmonary disease," Am. J. Respir. Crit. Care Medicine, May 15, 2002, 165(10):1404-1409.

Scher et al., "The lung microbiota in early rheumatoid arthritis and autoimmunity," Microbiome, Nov. 17, 2016, 4(1):60, 10 pages.

Statistical Power Analysis for the Behavioral Sciences, 2nd ed., Cohen (ed.), 1988, Chapter 10, 64 pages.

Taneja et al., "Role of HLA class II genes in susceptibility/resistance to inflammatory arthritis: studies with humanized mice," Immunol. Reviews, Jan. 2010, 233(1):62-78.

Vassallo et al., "Cellular and humoral immunity in arthritis are profoundly influenced by the interaction between cigarette smoke effects and host HLA-DR and DQ genes," Clin. Immunology, May/Jun. 2014, 152(1-2):25-35.

Wang et al., "Sputum microbiome temporal variability and dysbiosis in chronic obstructive pulmonary disease exacerbations: an analysis of the COPDMAP study," Thorax, Apr. 2018, 73(4):331-338.

Wright et al., "Animal models of cigarette smoke-induced chronic obstructive pulmonary disease," Expert Rev. Respir. Medicine, Dec. 2010, 4(6):723-734.

Yadava et al., "Microbiota Promotes Chronic Pulmonary Inflammation by Enhancing IL-17A and Autoantibodies," Am. J. Respir. Crit. Care Medicine, May 1, 2016, 193(9):975-987.

Yang et al., "Dysregulated Lung Commensal Bacteria Drive Interleukin-17B Production to Promote Pulmonary Fibrosis through Their Outer Membrane Vesicles," Immunity, Mar. 19, 2019, 50(3)1692-706.e7.

Oglesbee et al., "Second-tier test for quantification of alloisoleucine and branched-chain amino acids in dried blood spots to improve newborn screening for maple syrup urine disease (MSUD)," Pediatric Clinical Chemistry, 54(3):542-549, Mar. 2008.

\* cited by examiner

SEQUENCE LISTING

<160> NUMBER OF SEQ ID NOS: 2

<210> SEQ ID NO 1
<211> LENGTH: 58
<212> TYPE: DNA
<213> ORGANISM: Artificial Sequence
<220> FEATURE:
<223> OTHER INFORMATION: synthetic oligonucleotide primer

<400> SEQUENCE: 1
aatgatacgg cgaccaccga gatctacact atggtaattg tcctacggga ggcagcag        58

<210> SEQ ID NO 2
<211> LENGTH: 66
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: 37-48
<223> OTHER INFORMATION: n = any nucleic acid

<400> SEQUENCE: 2
caagcagaag acggcatacg agatgccgca ttcgatnnnn nnnnnnncc gtcaattcmt        60 ttragt                                                                  66

METHODS AND MATERIALS FOR ASSESSING AND TREATING ARTHRITIS

CROSS REFERENCE TO RELATED APPLICATIONS

This application is a divisional application of U.S. application Ser. No. 15/547,107, filed Jul. 28, 2017 (now U.S. Pat. No. 10,465,224), which is a National Stage application under 35 U.S.C. § 371 of International Application No. PCT/US2016/016385, having an International Filing Date of Feb. 3, 2016, which claims the benefit of U.S. Provisional Ser. No. 62/111,215 filed Feb. 3, 2015. The disclosures of the prior applications are considered part of (and are incorporated by reference in) the disclosure of this application.

BACKGROUND

1. Technical Field

This document relates to methods and materials involved in assessing and treating arthritis. For example, this document provides methods and materials for identifying arthritis patients as well as methods and materials for treating arthritis patients.

2. Background Information

Rheumatoid arthritis (RA) is an autoimmune disease that is characterized by inflammation of the synovial joints leading to joint destruction and deformities. Despite advances to understand the pathogenesis of RA, its etiology remains unknown. An infectious etiology of RA has been proposed for decades, although conclusive evidence between infections and onset of RA is absent.

SUMMARY

This document provides methods and materials involved in assessing mammals (e.g., humans) for arthritis. For example, this document provides methods and materials for assessing a mammal's gut microbial diversity to identify the mammal as having arthritis (e.g., rheumatoid arthritis). As described herein, mammals having an increase in gut microbial diversity of rarely represented genera (e.g., *Eggerthella, Collinsella, Rikenella,* and *Pseudomonas*) as compared to the diversity of rarely represented genera present in healthy controls (e.g., humans without arthritis) can be identified as having arthritis (e.g., rheumatoid arthritis). In some cases, mammals having a reduced abundance of *Faecalibacterium* (as compared to the abundance of *Faecalibacterium* present in healthy controls such as humans without arthritis) can be identified as having arthritis (e.g., rheumatoid arthritis).

This document also provides methods and materials involved in treating arthritis. For example, this document provides methods and materials for administering one or more agents to a mammal with arthritis to reduce the level of gut microbial diversity of rarely represented genera (e.g., *Eggerthella, Collinsella, Rikenella,* and *Pseudomonas*) within the mammal's gut. As described herein, mammals with arthritis can be treated with one or more agents (e.g., antibiotics or antibiotics followed by probiotic formulations) to reduce the level of gut microbial diversity of rarely represented genera (e.g., *Eggerthella, Collinsella, Rikenella,* and *Pseudomonas*) within the mammal's gut, thereby restoring a gut microbial diversity similar to that observed in control mammals (e.g., healthy humans without arthritis).

In general, one aspect of this document features a method for identifying a mammal as having arthritis. The method comprises, or consists essentially of, determining whether or not the gut of a mammal has an elevated level of gut microbial diversity of rarely represented genera, wherein the presence of the elevated level indicates that the mammal has arthritis, and wherein the absence of the elevated level indicates that the mammal does not have arthritis. The mammal can be a human. The arthritis can be rheumatoid arthritis. The method can comprise determining whether or not the gut of the mammal has an elevated level of gut microbial diversity of *Eggerthella, Collinsella, Rikenella,* or *Pseudomonas*. The gut can have an elevated level, and the mammal can be classified as having the arthritis.

In another aspect, this document features a method for treating arthritis. The method comprises, or consists essentially of, (a) identifying a mammal as having arthritis, (b) administering an antibiotic to the mammal to reduce the number of microbial organisms within the gut of the mammal, and (c) administering a formulation comprising live microbial organisms, wherein the formulation lacks species from the *Eggerthella, Collinsella,* and *Pseudomonas* genera. The step (c) can be performed between 2 days and 5 days after the step (b).

In another aspect, this document features a method for identifying a mammal as having arthritis. The method comprises, or consists essentially of, determining whether or not a mammal has an elevated level of beta-alanine, alpha-aminoadipic acid, hydroxylysine.2, asparagine, lysine, or cystine within plasma, wherein the presence of the elevated level indicates that the mammal has arthritis, and wherein the absence of the elevated level indicates that the mammal does not have arthritis.

In another aspect, this document features a method for identifying a mammal as having arthritis. The method comprises, or consists essentially of, determining whether or not a mammal has a reduced level of beta-aminoisobutyric acid, hydroxylysine.1, allo-isoleucine, citrulline, or glutamic acid within plasma, wherein the presence of the reduced level indicates that the mammal has arthritis, and wherein the absence of the reduced level indicates that the mammal does not have arthritis.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a principal correspondence plot representing the relationships between the OTU's and each sample category. Each symbol depicts one sample (squares indicate men, and circles indicate women). The microbiota of men and women are similar.

DETAILED DESCRIPTION

Figure 1:
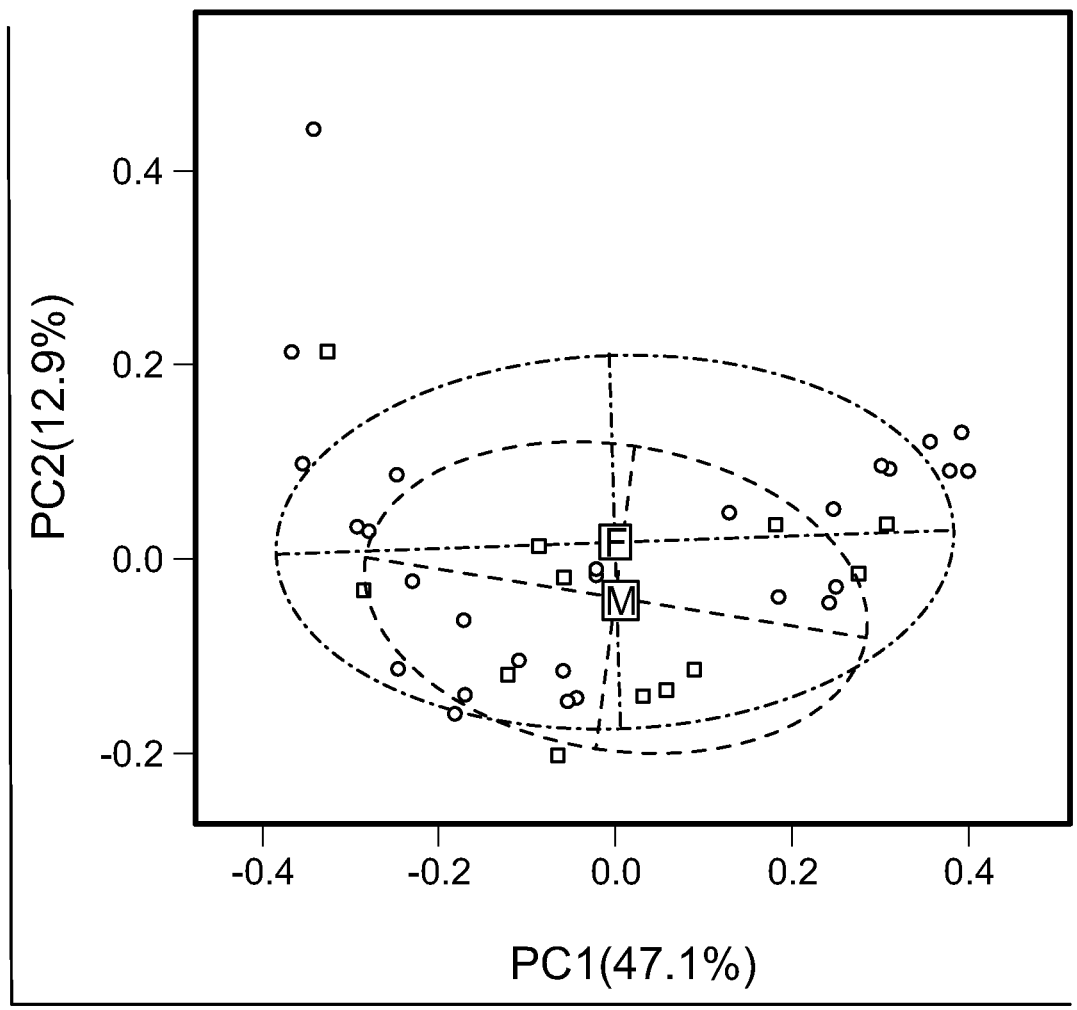

This document provides methods and materials involved in assessing and treating arthritis. For example, this document provides methods and materials for identifying arthritis patients as well as methods and materials for treating arthritis patients.

As described herein, a mammal having an elevated level of gut microbial diversity of rarely represented genera (e.g., *Eggerthella*, *Collinsella*, *Rikenella*, and *Pseudomonas*) within the mammal's gut can be classified as having arthritis. For example, a human having more species of *Eggerthella*, *Collinsella*, *Rikenella*, and/or *Pseudomonas* within the human's gut than the number of species typically observed within the gut of healthy humans can be classified as having arthritis (e.g., rheumatoid arthritis). Any appropriate method can be used to determine the level of gut microbial diversity of a mammal. For example, sequencing techniques such as those described herein can be used to determine the level of gut microbial diversity of a mammal.

In some cases, metabolite levels within plasma can be assessed to identify a mammal as having arthritis. For example, a mammal (e.g., a human) having an elevated level of beta-alanine, alpha-aminoadipic acid, hydroxylysine.2, asparagine, lysine, and/or cystine within plasma can be classified as having arthritis (e.g., rheumatoid arthritis). In some cases, a mammal (e.g., a human) having a reduced level of beta-aminoisobutyric acid, hydroxylysine.1, allo-isoleucine, citrulline, and/or glutamic acid within plasma classified as having arthritis (e.g., rheumatoid arthritis).

In some cases, the level of gut microbial diversity (e.g., the level of gut microbial diversity of rarely represented genera) and/or plasma metabolite levels (e.g., beta-alanine, alpha-aminoadipic acid, hydroxylysine.2, asparagine, lysine, cystine, beta-aminoisobutyric acid, hydroxylysine.1, allo-isoleucine, citrulline, and/or glutamic acid) can be used to identify mammal's having arthritis, can be used to monitor the progression of disease (e.g., progression of arthritis), can be used to identify mammal's having extra articular features and other cardiovascular complications, or can be used to identify mammal's having interstitial lung disease.

In some cases, once a mammal (e.g., a human) is classified as having arthritis (e.g., rheumatoid arthritis) as described herein, the mammal can be treated in a manner that improves the mammal's arthritis. For example, a mammal classified as having arthritis (e.g., rheumatoid arthritis) based at least in part on an elevated level of gut microbial diversity of rarely represented genera can be treated as described herein.

In some case, a mammal having arthritis (e.g., rheumatoid arthritis) can be treated with one or more agents (e.g., antibiotics or antibiotics followed by probiotic formulations) to reduce the level of gut microbial diversity of rarely represented genera (e.g., *Eggerthella*, *Collinsella*, *Rikenella*, and *Pseudomonas*) within the mammal's gut, thereby restoring a gut microbial diversity similar to that observed in control mammals (e.g., healthy humans without arthritis). For example, a mammal (e.g., a human) with arthritis (e.g., rheumatoid arthritis) can be treated with one or more antibiotics having the ability to kill rarely represented genera (e.g., *Eggerthella*, *Collinsella*, *Rikenella*, and *Pseudomonas*) within a mammal's gut. In some cases, a mammal having arthritis (e.g., rheumatoid arthritis) can be treated with one or more antibiotics to kill most of the microbial organisms present within a mamma's gut. After a period of time (e.g., about 2 days to about 5 days), the mammal (e.g., human) can be treated with a probiotic formulation designed to repopulate the mammal's gut with a population of microbial organisms that does not include species from one or more of the following genera: *Eggerthella*, *Collinsella*, *Rikenella*, and *Pseudomonas*. Examples of probiotic formulations that can be used to repopulate a mammal's gut when treating arthritis include, without limitation, those formulations that contain *Prevotella*, *Faecalibacterium* and/or *Lachnobacterium*. In some cases, a probiotic formulation that can be used to repopulate a mammal's gut when treating arthritis can contain *Prevotella*, *Faecalibacterium* and/or *Lachnobacterium*, and no other type of microbial organism.

In some cases, a probiotic formulation can be administered once or multiple times to treat a mammal having arthritis. For example, a probiotic formulation lacking species from *Eggerthella, Collinsella, Rikenella,* and *Pseudomonas* can be administered from once a day to once every other month. In some cases, a probiotic formulation can be administered every other day.

The invention will be further described in the following examples, which do not limit the scope of the invention described in the claims.

EXAMPLES

Example 1—Rheumatoid Arthritis Gut Microbiota is Characterized by an Expansion of Rare Lineage Microbes Normally Present in Healthy Individuals Patients attending the Rheumatology clinic at Mayo clinic that fulfilled the exclusion and inclusion criteria were asked for enrollment in the study. Adult patients (18 years or older) who met the American College of Rheumatology (ACR) 2010 classification of RA were recruited after their informed consent.

Patient's disease activity scores, joint counts, presence of autoantibodies (rheumatoid factor (RF) and anti-citrullinated peptide antibodies (ACPA)), and history of drugs (i.e., disease modifying anti-rheumatic drugs (DMARDs) such as methotrexate, hydroxychloroquine, and Leflunomide, and biologic drugs such as rituximab, tocilizumuab, etanercept, adalimumab, anakinra, abatacept, and infliximab) and prednisone were collected. The demographic of the study population was determined (Table 1). The study included 40 patients with rheumatoid arthritis and 32 controls (15 first degree relatives and 17 random healthy controls). The median (interquartile range (IQR)) age of subjects with RA was 54 years and of controls was 52 years. Seventy percent of the subjects and 81 percent of the controls were female. Eighty percent of patients were rheumatoid factor positive, and 83 percent were anti-citrullinated protein antibody (ACPA) positive. The median disease (IQR) duration was 47.5 months. Overall, patients had low disease activity with a median (IQR) DAS 28 of 2.6 (2.0, 4.3) and moderate disability with a median (IQR) HAQ score of 0.5 (0.1, 1.1). The majority of patients (61 percent) were taking methotrexate. Almost half of the patients (49 percent) were taking prednisone, and 34 percent were on a biologic response modifier (10 patients were on an anti-TNF agents, 3 patients were on Abatacept, and 4 on rituximab).

TABLE 1

Demographic data of the study population.

| | RA (n = 40) M, (Med) inter Q | Control (n = 32) |
|---|---|---|
| Age, years, mean (median) | 55.7 (54) | 53 (52) |
| Female, % | 70% | 81% |
| BMI | 30.4 (30.1) | 30.9 (30.6) |
| HLA-DR4 | 52.5% | NA |
| Disease activity parameters | | |
| Disease duration, months, mean (median) | 81.6 (47.5) | |
| DAS28 | 3.15 (2.6) 1.96-4.3 | |
| HAQ | 0.6 (0.5) 0.12-1.12 | |
| ESR, mm/hour, mean | 18.5 (11) 5-23 | |
| CRP, mg/L, mean | 12.7 (3.6) 3-8.6 | |
| Patient VAS pain, mm, mean (median) | 37.28 (28) 12.75-49.5 | |
| TJC-28, mean (median) | 4.24 (1) 0-6 | |
| SJC-28, mean (median) | 4.28 (2) 0-8 | |
| Autoantibody status | | |
| RF positive, % | 100% | |
| ACPA positive, % | 83% | |
| RF titer, kU/L, mean (median) | 113 (63) 15-164 | |
| ACPA titer, kAU/L, mean (median) | 110 (99) 16-250 | |
| Medication use | | |
| Methotrexate, % | 61.2% | |
| Prednisone, % | 48.9% | |
| Biological agent, % | 34% | |

At the time of enrolling, patients were given an option to enroll any first degree relatives who consented and did not have any symptoms of inflammatory arthritis or other autoimmune diseases. These enrolled first degree relatives were used as controls. Other controls included sex and age matched healthy individuals with no known history of any autoimmune diseases. Any patient or control on antibiotics, consuming probiotics or known history of inflammatory bowel disease or other autoimmune diseases like diabetes or multiple sclerosis were excluded.

Sample Collection and DNA Extraction

Fecal samples were frozen within 24 hours of being obtained. Microbial DNA was extracted from samples using the MoBio PowerSoil Kit (MoBio Laboratories, Carlsbad, Calif., USA).

16S Amplicon Preparation and Sequencing

Polymerase chain reaction (PCR) was performed used 50 ng gDNA and 0.3 μM V3-V5 barcoded primers targeting 357F and 926R (5'-AATGATACGGCGACCACC-GAGATCTACACTATGGTAATTGTCCTACGGGAG GCAGCAG-3' (SEQ ID NO:1) and 5'-CAAGCAGAA-GACGGCATACGAGATGCCGCATTCGATXXXXXXX-XXXXXCCGTCAATTCMTTTRAGT-3' (SEQ ID NO:2)) with Kapa HiFi Hotstart Ready Mix (Kapa Biosystem). PCR conditions were set to 95° C. for 3 minutes, 35 cycles of 98° C. for 30 seconds, 70° C. for 15 seconds, and 72° C. for 15 seconds, and finally 72° C. for 5 minutes in a Bio-Rad T100 Thermal Cycler. PCR product sizes were verified using Agilent Tape station with reaction cleanup and concentration performed using epMotion automated system (Eppendorf) with Agencourt AMPure PCR Purification System. Final quantitation was performed using the QuBit HS dsDNA kit with a QuBit 2.0 flurometer (Life Technologies). Samples were pooled to equal concentration, and then sequenced on one lane of MiSeq using a MiSeq Reagent Kit v2 (500-cycles) (Illumina Inc., San Diego, Calif.), generating 20 million 2×250 base pair reads.

Pipeline for Processing of 16S Data

Pre-processed sequence files were then subjected to quality filtering using Trimmomatic version 0.22, with a hard cutoff of PHRED score Q3 for 5' and 3' ends of the reads (parameters LEADING:3 and TRAILING:3), trimming of the 3' end with a moving average score of Q15 with a window size of 4 bases (parameter SLIDINGWINDOW:4:15), and removing any remaining reads shorter than 75% of the original read length (parameter MINLEN:112 for reads of 150 bp long). Finally, reads with any ambiguous base calls or with homopolymers longer than 10 bases longs were discarded using Mothur. Only the read pairs that survived the quality filter were processed further. Any surviving reads that were unpaired (i.e., they lost their matching pair due to low quality) were discarded. Surviving read pairs were then grouped into two files, one each for 'read 1' and 'read 2' sequences. Reads also were de-replicated, consolidating identical reads to avoid redundant processing. Each of the two read libraries then was checked for chimeras using UCHIME in de novo mode.

Taxonomy Assignment

To prepare the reads for taxonomic assignment, reads from the previous step just before the stitching procedure were used by removing the gaps and then stitching them with a pad sequence of "N" bases. Since by default most Bayesian classifiers use 8-mers to perform the classification, "NNNNNNNN" was used as the padding. The stitched reads were then classified using the Green genes taxonomy (version 13.5).

Clustering, Representative Sequences, and Chimera Removal

Paired-end reads were concatenated directly with no padding and de-replicated. Operational taxonomic unit (OUT) representatives were selected and used to generate a reference set for clustering using UPARSE run with default parameters that also removed chimeric reads.

α-Diversity Analysis

For observed number of OTUs, Shannon and inverse Simpson diversity indices were calculated based on the rarefied OTU counts to address differential sequencing depths (estimate richness' function in Bioconductor package 'PhyloSeq'). Rarefaction curves were created by rarefying the OTU counts to different sequencing depths. A simple linear model was used for testing the association between α-diversity measures and variables of interest adjusting for other covariates such as gender.

β-Diversity Analysis

Unweighted, weighted, generalized UniFrac, and Bray-Curtis distances were constructed using the OTU table and the phylogenetic tree ('GUniFrac' function in R package 'GUniFrac'). Rarefaction was performed on the OTU table before calculating the distances. Based on these distance matrices, PERMANOVA was used to test for association between variables of interest and the overall microbiota composition adjusting for other covariates ('adonis' function in R package 'vegan'). PERDISP2 was used for testing the homogeneity of group dispersions ('betadisper' function in R package 'vegan'). Significance was assessed by 1,000 permutations for all these distance-based methods. Principle Coordinate Analysis was performed on the distance matrix ('cmdscale' function in R), and the first two Principal Coordinates (PCs) were used to generate the ordination plots.

Differential Abundance Analysis

Non parametric Wilcox Rank Sum test was used for testing group difference in taxa abundances at the phylum, family, and genus level. A false discovery rate (FDR) control based Storey's value procedure was used to correct for multiple testing (p, q value in R). To reduce the number of tests, the analysis was confined to taxa with prevalence >10% and maximum proportion >0.002. FDR control was performed on each taxonomic rank. An adjusted p-value or q-value less than 0.15 was considered to be statistically significant. Differential abundance analysis was visualized using the LEfSe software with a nominal p-value of 0.05 and a logarithmic LDA score of 2 as threshold.

Predictive Model for RA Development Using Random Forests

Machine learning algorithm Random Forests (RF) was used to classify the subjects into two classes (RA and control) based on their microbiota profile using default parameters of the R implementation of the algorithm (R package 'random Forest', ntree=200, mtry=8). The RF algorithm, due to its non-parametric assumptions, was able to detect both linear and nonlinear effects and potential taxon-taxon interactions, thereby identifying taxa that discriminate RA subjects from control subjects. The genus-level proportion data for the 66 genera served as input data. Bootstrapping was used to assess the classification accuracy, where the bootstrapped samples were used as a training set and the unused samples as a test set. The classification performance was compared to random guess, where the class label for the samples in the test set was predicted to be the class label of the majority class in the training set, and Friedman Rank Sum test was used for testing the significance of the difference. Boruta variable selection was applied for selecting the most discriminatory taxa based on the importance values produced by RF. The importance value of a genus was calculated based on the loss of accuracy by the random permutation of the abundance profile of the genus. The Boruta method used spiked-in 'shadow' taxa, which were shuffled versions of real taxa, to assess whether the importance was significant.

Metabolomic Data Analysis

The amino acids and metabolites from plasma were measured by LC/MS/MS on Quantum Ultra and Agilent 6460 QQQ. The metabolites (carnitine, TMA, TMAO, betaine, and choline) were measured by MS/MS on API5000. The metabolomic data were first subjected to normal transformation before the analysis to meet the normality assumption of the statistical tests. Principle component analysis was used to reduce the dimensionality of the metabolomic data, and the subjects were projected on the first two principle components to visualize their relationships. The PERMONOVA test was used to test for the overall difference of the metabolomic profiles between RA and their relatives based on Euclidean distance. Two-sample Student's t test was then used to identify differential metabolites between RA patients and their relatives or between genders. False discovery control was used to correct for multiple testing. The metabolite PC1, which summarizes the overall metabolome variation pattern, was tested for association between the metabolome and microbiota within the RA samples. The differential metabolites between RA and their relatives also were tested for specific association with the microbiota using distance-based PERMANOVA test within RA patients. The specific associations between these differential metabolites and taxa also were investigated using the Spearman's rank correlation test. All the statistical analyses were performed in R-3.0.2 (R Development Core Teams).

Collagen-Induced Arthritis (CIA) and Treatment with *Collinsella*

HLA-DQ8.AEo mice were used (Taneja et al., *Arthritis Rheum.*, 56:69-78 (2007) and Taneja and David, *Immunol. Rev.*, 169:67-79 (1999)). Briefly, CIA was induced in transgenic animals by immunization with 100 μL of type II collagen (CII) (100 μg of CII emulsified in 1:1 ratio of complete Freund's adjuvant) injected at the base of tail. DQ8 mice (N=18) were immunized with type II collagen, and 2 weeks later, 10 mice were treated with *Collinsella* alternate days for four weeks. Arthritis onset and progression was monitored. The arthritic severity of mice was evaluated with a grading system for each paw of 0-3 (Taneja et al., *Arthritis Rheum.*, 56:69-78 (2007)). The mean arthritic score was determined using arthritic animals only.

Mice were immunized with 200 μg of CII emulsified 1:1 in CFA (Difco) intradermally at the base of the tail. Ten days post-immunization, spleens were removed, and cells were harvested. Splenic T cell responses were evaluated by culturing cells with CII and testing proliferation using $^3$H-thymidine incorporation. The T cell response was evaluated with CD4 T cells sorted from splenic CII-primed DQ8 mice cultured in vitro in the presence or absence of CII (50μg/mL) and DCs (pre-cultured with bacteria or supernatant of the bacterial culture). T cell proliferation was assessed using routine $^3$H-thymidine incorporation (Taneja et al., *Arthritis Rheum.*, 56:69-78 (2007)). The difference in the incidence of arthritis between groups was analyzed using Fisher's exact test. All other significance values were calculated using the Student's t test or T test with unequal variance.

Staining for Tight Junction Proteins

Human intestinal epithelial cell line CACO-2 was grown in vitro. Expression of tight junction protein zonulin-1 (Zo-1) was tested by immunofluorescence using purified anti-zonulin-1 antibody (Life Technologies) as primary and FITC conjugated anti-rabbit IgG (Jackson ImmunoResearch Laboratories) as secondary antibody.

Disease Duration and Seropositivity is Associated with Decreased Diversity

Figure 2:
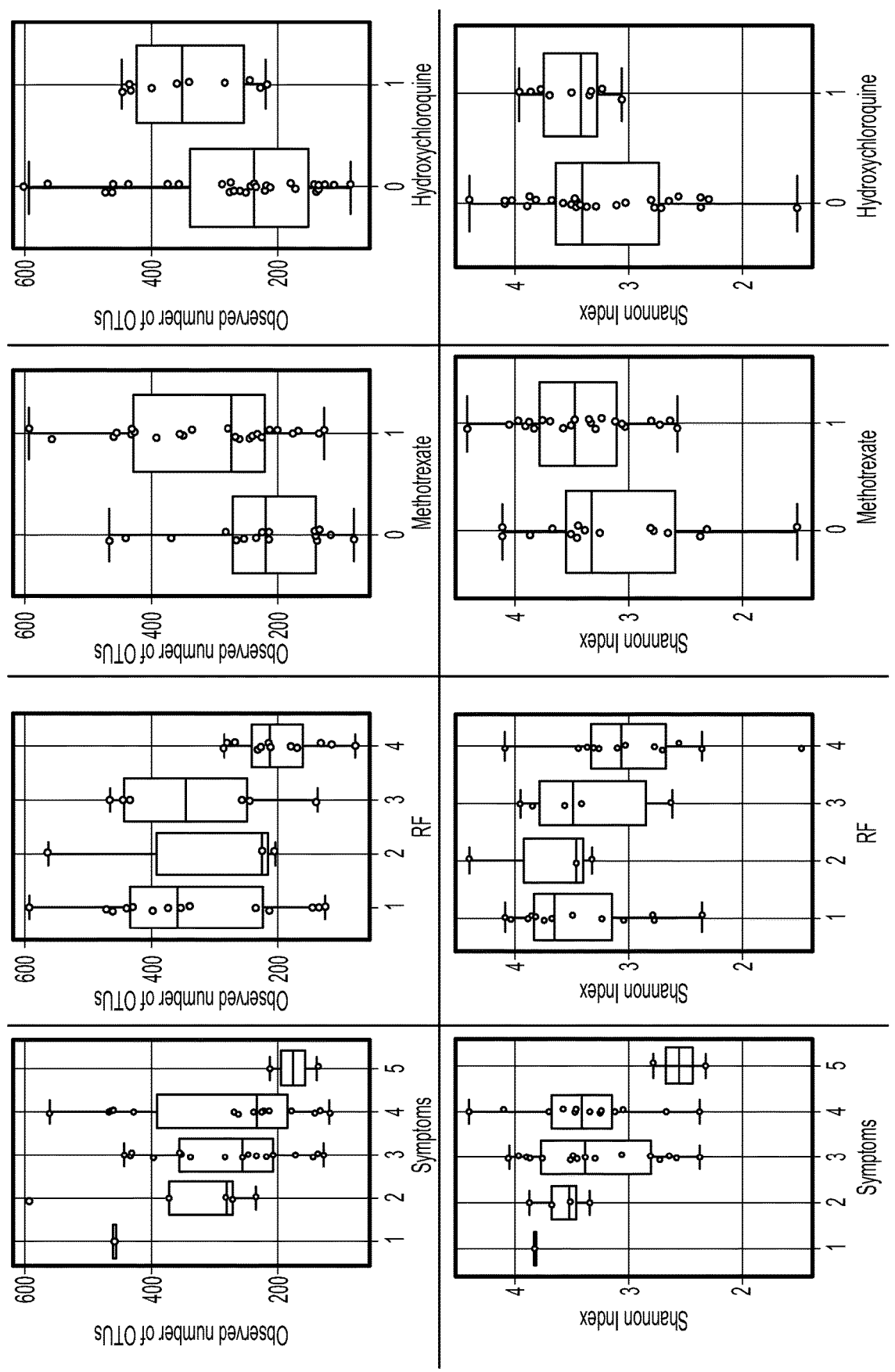
FIG. 2 contains graphs demonstrating that symptom severity and autoantibodies correlate with decreased alpha-diversity. Alpha diversity was calculated by comparing observed numbers of OTUs (N=40) and community composition diversity by Shannon Index. RF=Rheumatoid factor: 1=<25, 2=25-50, 3=50-100, and 4=>100. Symptoms-Duration of disease, 1=<6 months, 2=>6 months, 3=>1 year, 4=2-5 years, and 5=>5 years. Methotrexate and hydroxycholine, 0=not treated with specific drug, and 1=treated with drug.
Figure 3:
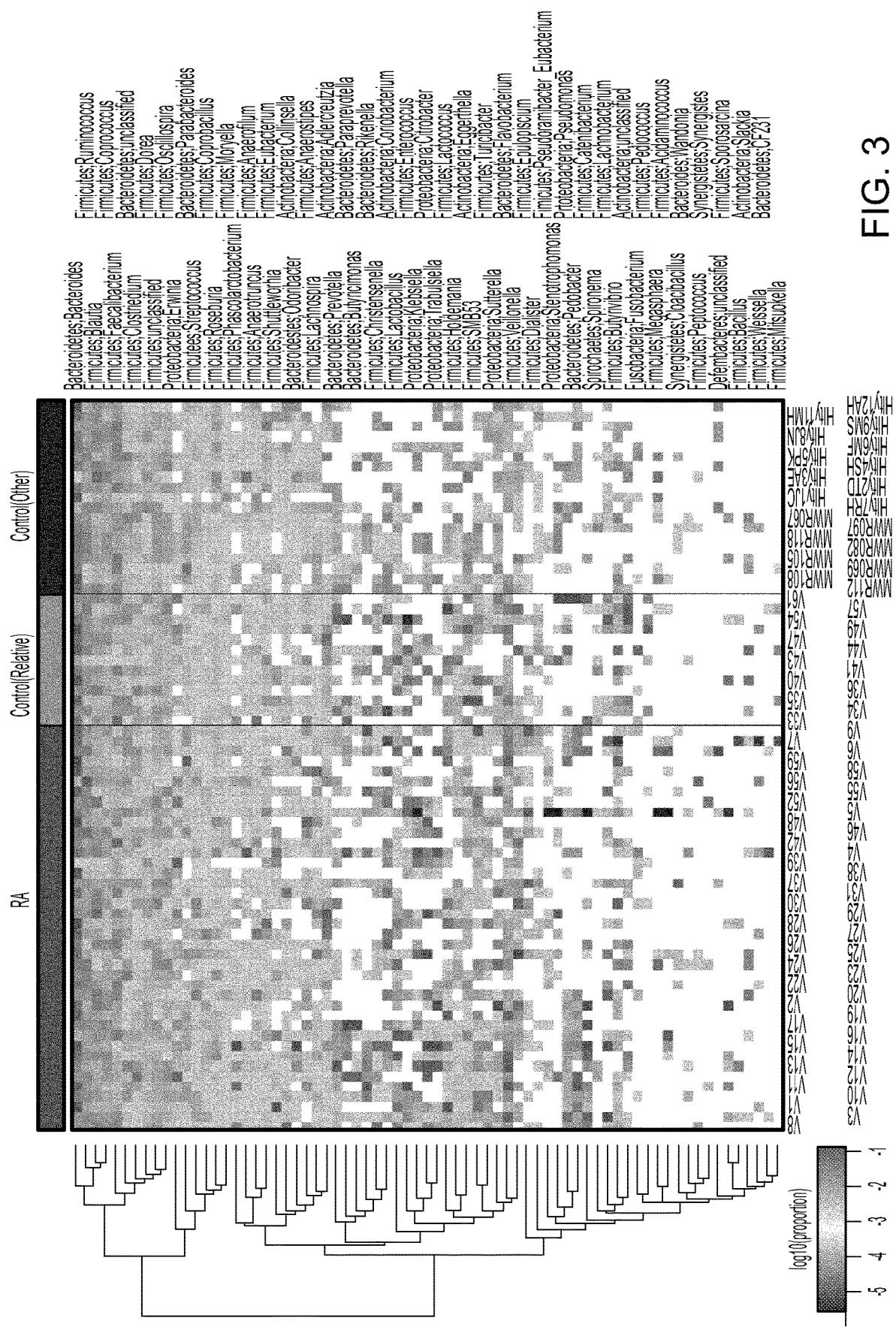
FIG. 3 is a heatmap for genus level abundance.

To determine if disease duration and autoantibodies are associated with a change in microbial diversity, V3-V5 regions of 16S gene of 40 fecal samples of RA patients fulfilling ACR 2010 criteria (Table 1) were sequenced. High quality sequences were analyzed (sequence lengths ranged from 21,045 to 894,587 with a 122,028 median sequence length). A total of 2188 operational taxonomic units (OTUs), after removing singletons (median of 54 and with range of 2-686,387) clustered at 97% sequence similarity, were used to assign taxonomic identification and calculate bacterial abundance in fecal communities. First, the microbial diversity was determined within the patient group according to bone mass index (BMI) (Table 2). These results demonstrated a decreased diversity of the gut microbiota with increased BMI (P=0.025). RA patients exhibited similar microbial diversity and richness, suggesting sex bias reported in healthy humans is lost (FIG. 1). Clinical features were correlated with the microbial diversity and richness by the observed numbers of OTUs and Shannon index (FIG. 2). Increasing levels of RF and disease duration were associated with decreased alpha-diversity and richness. Patients using MTX and Hydrochloroquine exhibited an increase in alpha diversity, indicating restoration of normal microbiota after treatment. Treatment with Prednisone, on the other hand, did not have any effect of the diversity of OTUs. There was no difference in the overall diversity and abundance of OTUs in the context of DR4, radiographic erosions, and HAQ score (FIG. 3).

Figure 14:
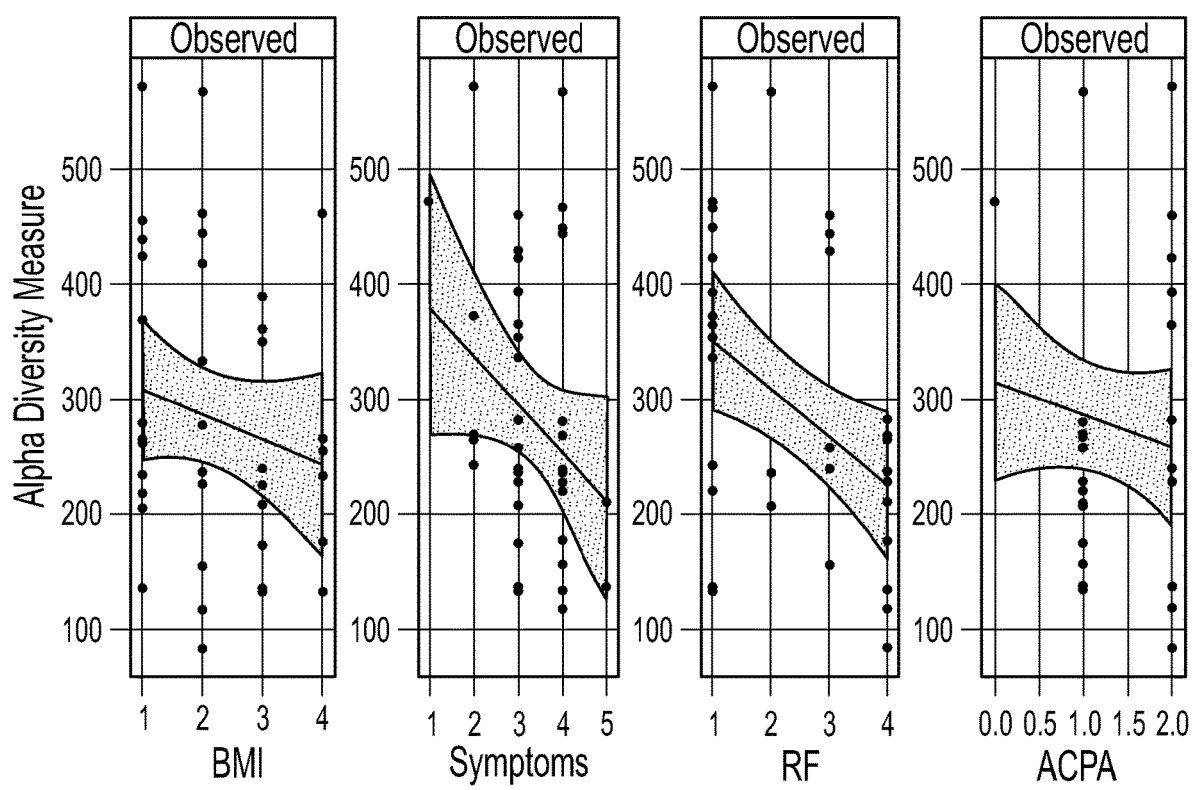
FIG. 14. Decreased diversity is associated with increase in disease onset, rheumatoid factor (RF), and anti-citrullinated antibodies (ACPA). Body mass index (BMI) was associated with decreased species richness in the gut microbiota of RA patients. Species richness was measured by the observed OTU numbers and calculated on the rarefied counts. The dashed line shows the fitted linear regression line with the gray area indicating the 95% confidence band. The three horizontal lines of the box represents the first, second (median), and third quartile respectively with the whisk extending to 1.5 inter-quartile range (IQR). BMI: 1, ≤24; 2, ≤30; 3, ≤35; and 4, ≤40.

Decreased diversity was associated with increase in disease onset, rheumatoid factor (RF), and anti-citrullinated antibodies (ACPA) (FIG. 14). Body mass index (BMI) was associated with decreased species richness in the gut microbiota of RA patients (FIG. 14).

Gut Microbiota of RA Patients Differs from First Degree Relatives and Healthy Controls To determine if RA patients have a dysbiotic gut microbiota, 16S gene of 40 RA patients and 32 fecal samples (15 first degree relatives with no autoimmune disease, and 17 randomly enrolled healthy controls (HCs)) were sequenced. The OTUs were classified into 13 phyla, 26 classes, 40 orders, 76 families, and 157 genera, and diversity and abundance of various genera were plotted in heatmap (FIG. 3).

Figure 4:
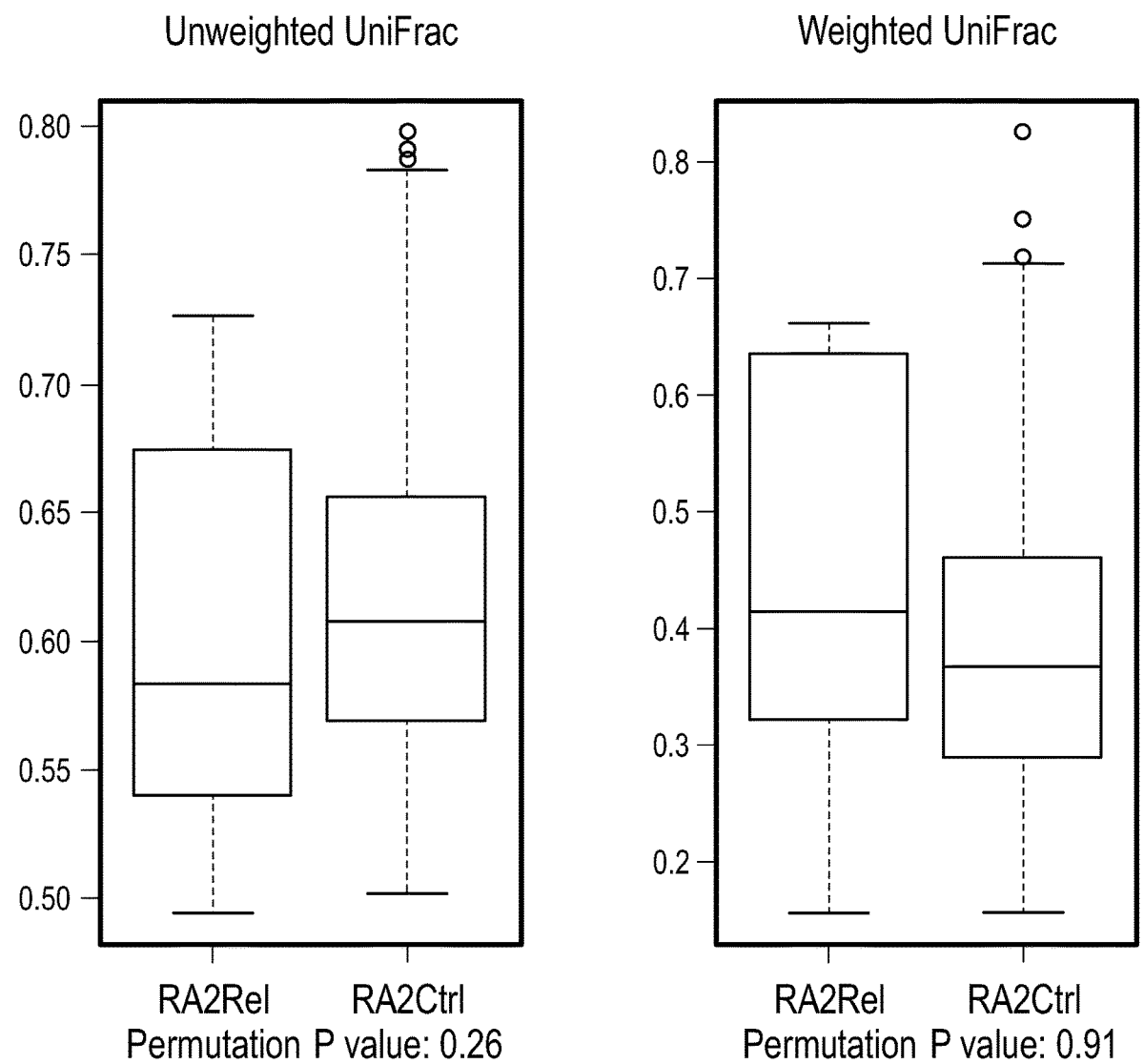
FIG. 4 contains graphs demonstrating that microbiota of relatives are not significantly different from the other healthy controls (p=0.14 and 0.34 for unweighted and weighted UniFrac).

To test whether the microbiota of relatives were similar to healthy controls (HCs), UniFrac (unweighted, weighted and generalized) distances between relatives were compared to those between relative and other controls. The three UniFracs had different power in detecting types of community changes. Unweighted UniFrac distance was more powerful to detect community structure change or change in rare lineages while weighted UniFrac was used for detecting changes in abundant lineages. Generalized UniFrac distance struck a balance between unweighted and weighted UniFracs. OTUs from the abundant genera (weighted unifrac) as well rare genera (unweighted unifrac) were present with similar alpha and beta diversity and abundance suggesting that the microbiota of the relatives were not significantly different from the other healthy controls (p=0.14 and 0.34 for unweighted and weighted UniFrac) (FIG. 4). Therefore, these RA relatives were treated as independent samples and pooled with other healthy controls.

Figure 6A:
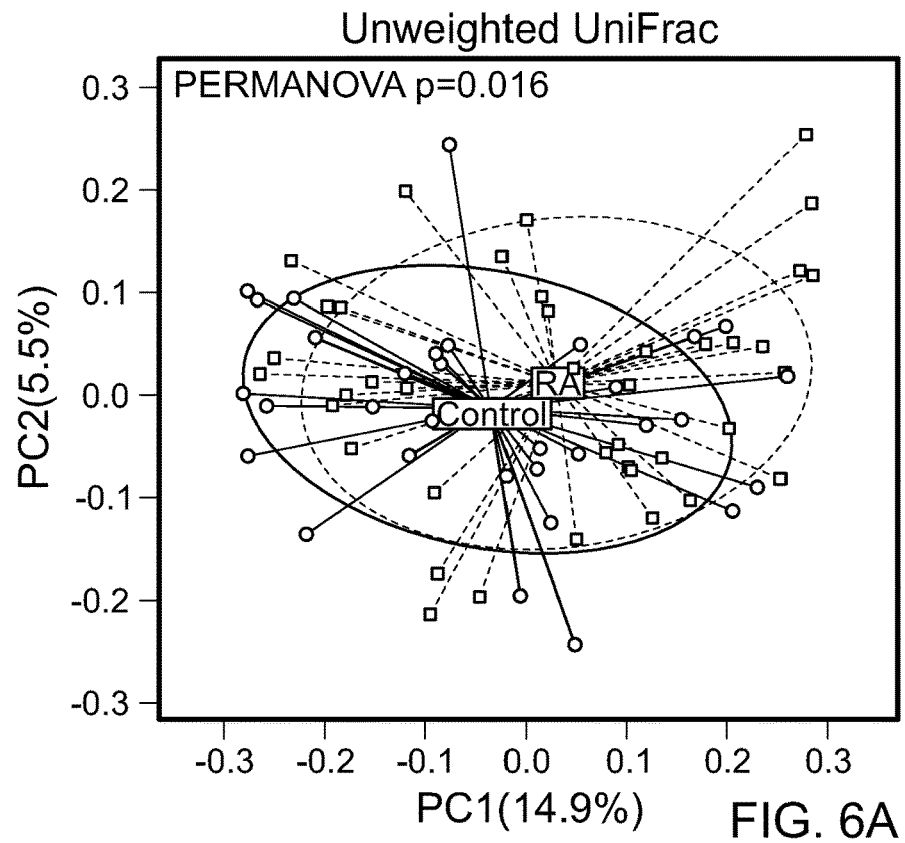
FIGS. 6A and 6B. The microbiota of the RA patients is different from healthy controls. (A) Principal correspondence plot reveals the relationship between the defining OTUs in RA and controls. The square symbols and their lines indicate RA patients, and the circular symbols and their lines indicate controls. The lines indicate vectors representing the relationships between the OTU's and each sample category. The vectors point to the center of gravity of the samples where OTU's mostly occur. The distance between the tip of the vector and the samples provides an indication of the probability of OTU content in each sample (point). The microbiota of RA subjects was significantly different from that of healthy controls. PERMANOVA p values: 0.016, 0.072, and 0.322 for Unweighted, generalized UniFrac, and weighted UniFrac, respectively. (B) The microbiota of RA subjects are more over-dispersed (Weighted UniFrac, p=0.12). The median within group distance was 0.43 within RA and 0.39 within Control (N=72: 40 RA patients and 32 controls).
Figure 6B:
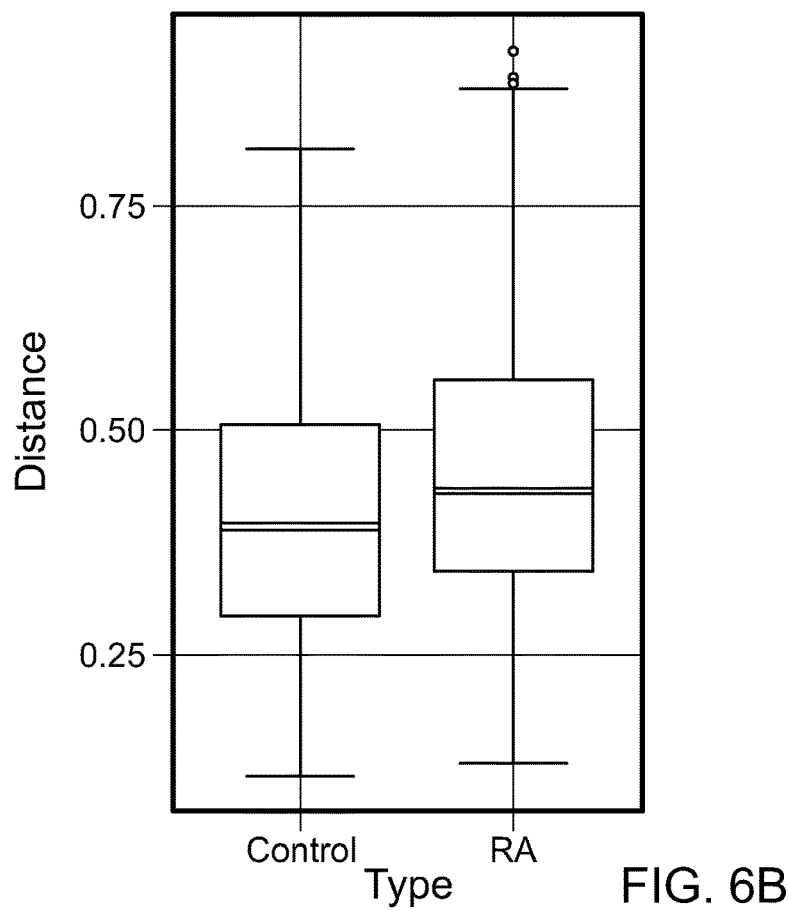
Figure 12A:
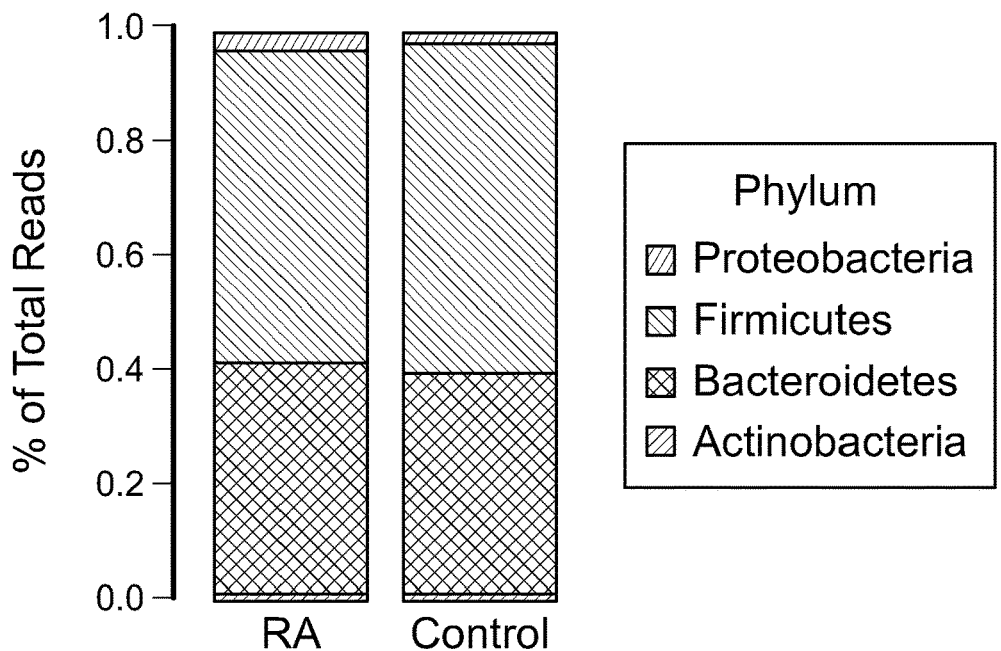
FIGS. 12A-G. The gut microbiota of RA patients differs from controls. (A) Percent of 16S reads of major phyla of the gut microbiota of RA patients and controls. Rarefaction curves comparing (B) the species richness (observed OTU numbers) and (C) the overall diversity (Shannon diversity index) of RA patients and controls. The microbiota of RA patients exhibits significantly lower diversity. The relative numbers of observed OTUs in RA patients and controls revealed a decrease in species richness in RA patients as compared to controls (p=0.003). (D-F) PCoA plot based on the Bray-Curtis distance matrix constructed using OTUs from all phyla (D), Firmicutes (E), Bacteroidetes (F), and Actinobacteria (G). The percentage of variability explained by the corresponding coordinate is indicated on the axis. Each point represents a sample, red symbols indicate RA patients and blue symbols indicate controls. The blue lines indicate vectors representing the relationships between the OTUs and each sample category. The ellipses serve a visual guide to group differences.
Figure 12B:
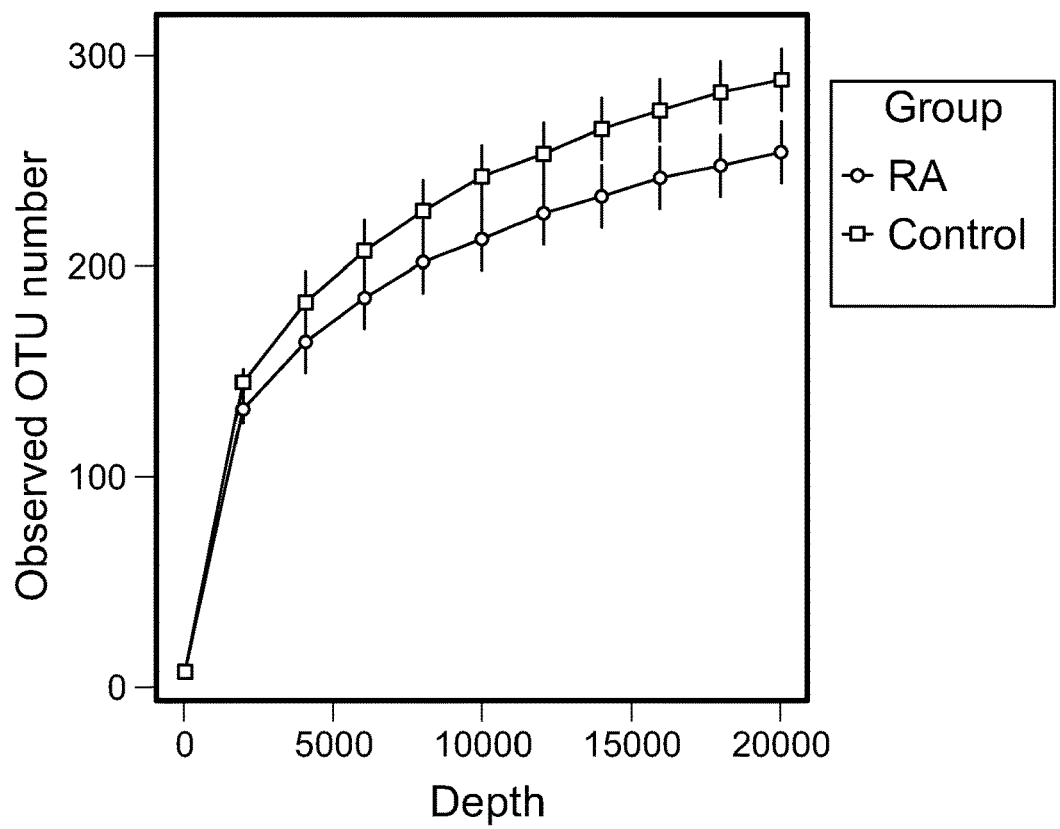

RA patients revealed a significant decrease in the alpha diversity compared to controls as observed by using Shannon index (p=0.003) (FIG. 12B). Overall diversity between RA patients and controls was comparable by Shannon Diversity index, suggesting that the most taxa most commonly present in humans are similar between the groups. To compare the taxa that occur with less abundance in humans, the bacterial community structure and difference in the rare represented taxa were analyzed in both groups. Dimension 1 of a CA plot describing the level of similarities and differences with specific OTUs explained 14.9% of the total variation in the data with significant permutational multivariate analysis of variance (PERMANOVA), P=0.01, suggesting differences in the presence and richness of the rare taxa (FIG. 6A). The overall community structure of RA patients revealed a trend towards over dispersion compared to controls (Weighted UniFrac, p=0.12.median within RA=0.43 and within controls=0.39; FIG. 6B). Collectively these data demonstrate that RA patients differ from controls in the presence rare lineages, while the common taxa in human microbiome are similar between the groups.

TABLE 2

Correlation of the RA microbiota with clinical features by alpha (top) and beta (bottom) diversity.

|  | Symptoms | HAQ | RF | ACPA | CRP | BMI | MTX | Prednisone | Hydroxychloroquine | HLA-DR4 |
|---|---|---|---|---|---|---|---|---|---|---|
| Observed # of OTUs | 0.09 | 0.765 | 0.029 | 0.286 | 0.342 | 0.025 | 0.035 | 0.22 | 0.056 | 0.437 |
| Shannon index | 0.145 | 0.281 | 0.067 | 0.748 | 0.545 | 0.328 | 0.082 | 0.072 | 0.139 | 0.613 |
| UniFrac | 0.524 | 0.713 | 0.259 | 0.449 | 0.058 | 0.018 | 0.101 | 0.343 | 0.059 | 0.615 |
| GUniFrac | 0.154 | 0.251 | 0.308 | 0.384 | 0.231 | 0.015 | 0.31 | 0.383 | 0.05 | 0.86 |
| WUniFrac | 0.216 | 0.202 | 0.203 | 0.452 | 0.303 | 0.092 | 0.534 | 0.47 | 0.111 | 0.697 |

Figure 12C:
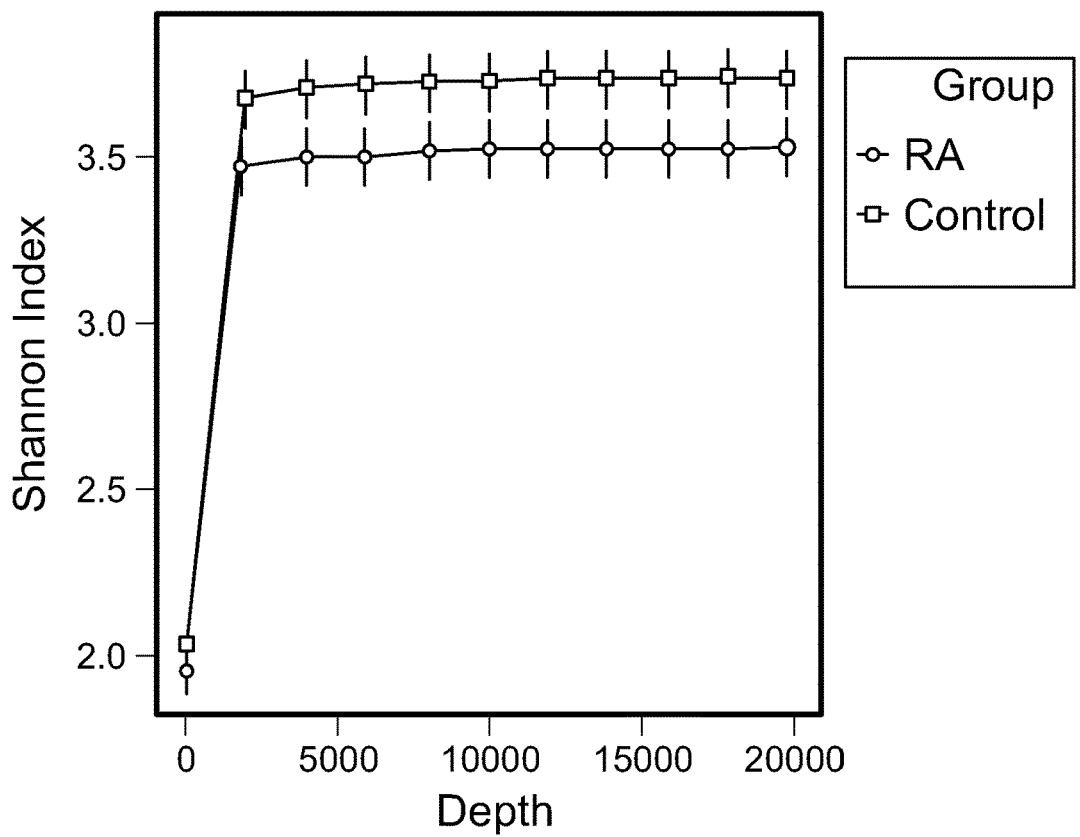
Figure 12D:
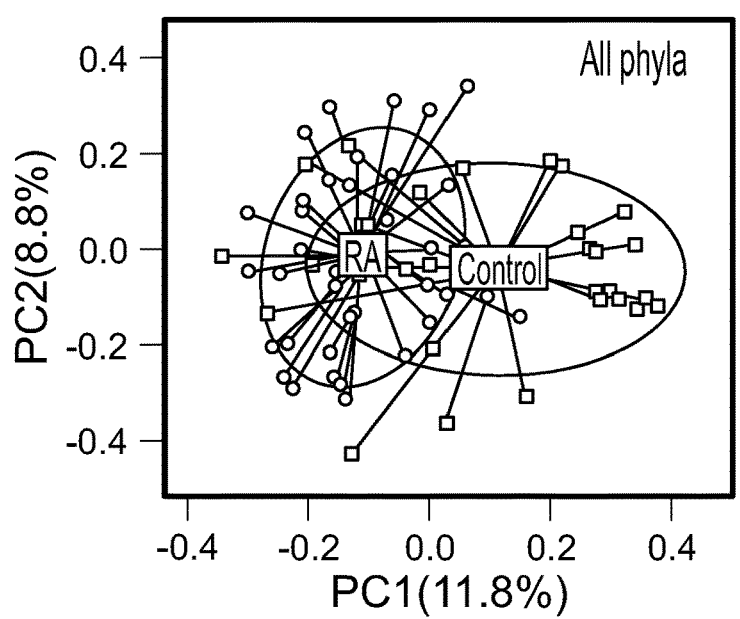
Figure 12E:
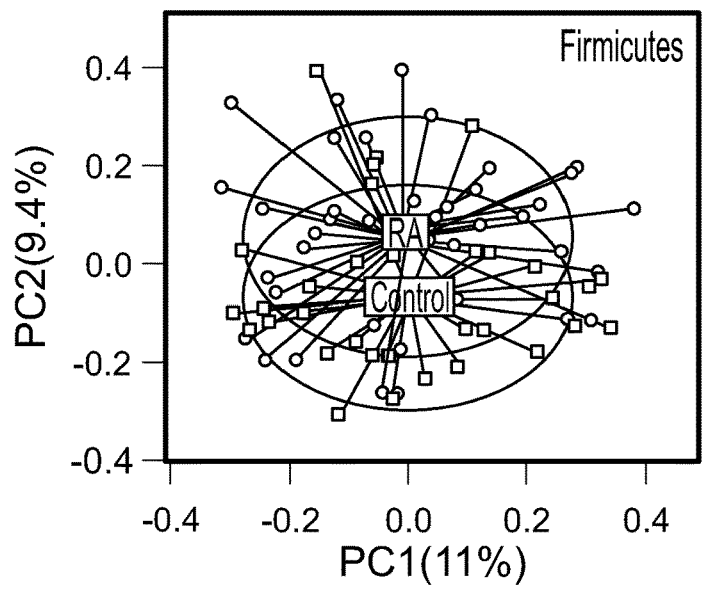
Figure 12F:
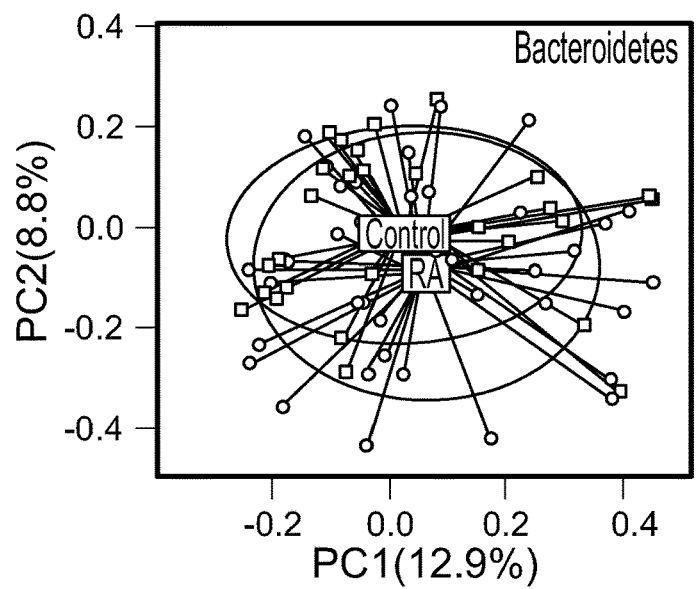
Figure 12G:
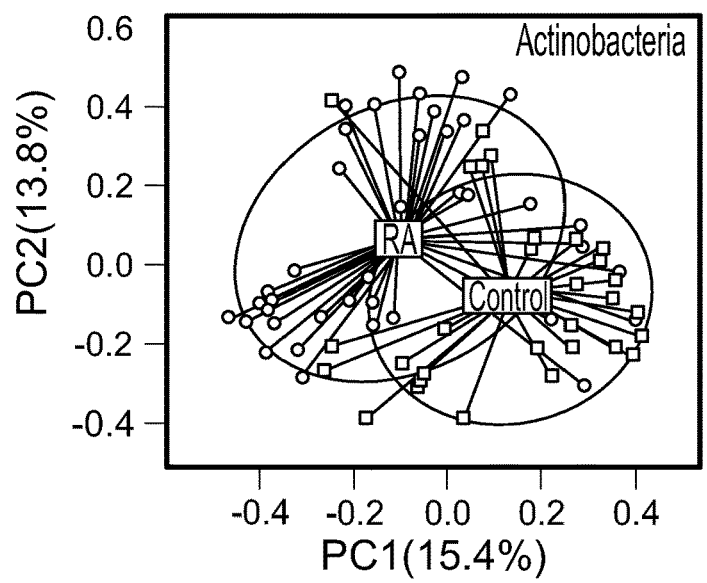

The phylum-level profiles for patients with RA and non-RA controls were rather similar, with the exception of increased number of reads from the phylum Actinobacteria in the RA group (0.45% vs 0.04%, respectively; FIG. 12A). Patients with RA exhibited a significant decrease in gut microbial diversity compared to non-RA controls as observed by a decrease in OTUs and a smaller Shannon diversity index (P<0.05) (FIGS. 12B and 12C). Permutational Multivariate Analysis of Variance (PERMANOVA) analysis based on Bray-Curtis distance showed that the structure of the microbiota of RA patients differed significantly from that of comparator subjects (PERMANOVA P<0.001, 1000 permutations, FIG. 12D). To assess the contribution of specific gut phyla to the observed microbiota difference, Bray-Curtis distances were constructed using OTUs from specific phyla. Principal coordinate analysis (PCoA) based on phylum-specific Bray-Curtis distances revealed that microbiota from patients with RA and non-RA controls differed much more in the low-abundant phylum, Actinobacteria, than in the two dominant phyla, Firmicutes and Bacteroidetes (FIGS. 12E and 12G).

Abundance of *Eggerthella lenta* is Associated with RA

A percentages-species contribution analysis (SIMPER) and Taxonomic search using RDP and NCBI databases was performed to identify the phylum, family, and genus and characterize the relative abundance distributions of the OTUs belonging to taxa with a prevalence of >10% and a maximum proportion of >0.002. A total of 8 phyla, 37 families, and 66 genera were tested. At false discovery rate of 15%, 11 differentially expressed abundant taxa were identified, particularly at the family level (Table 3).

Figure 7:
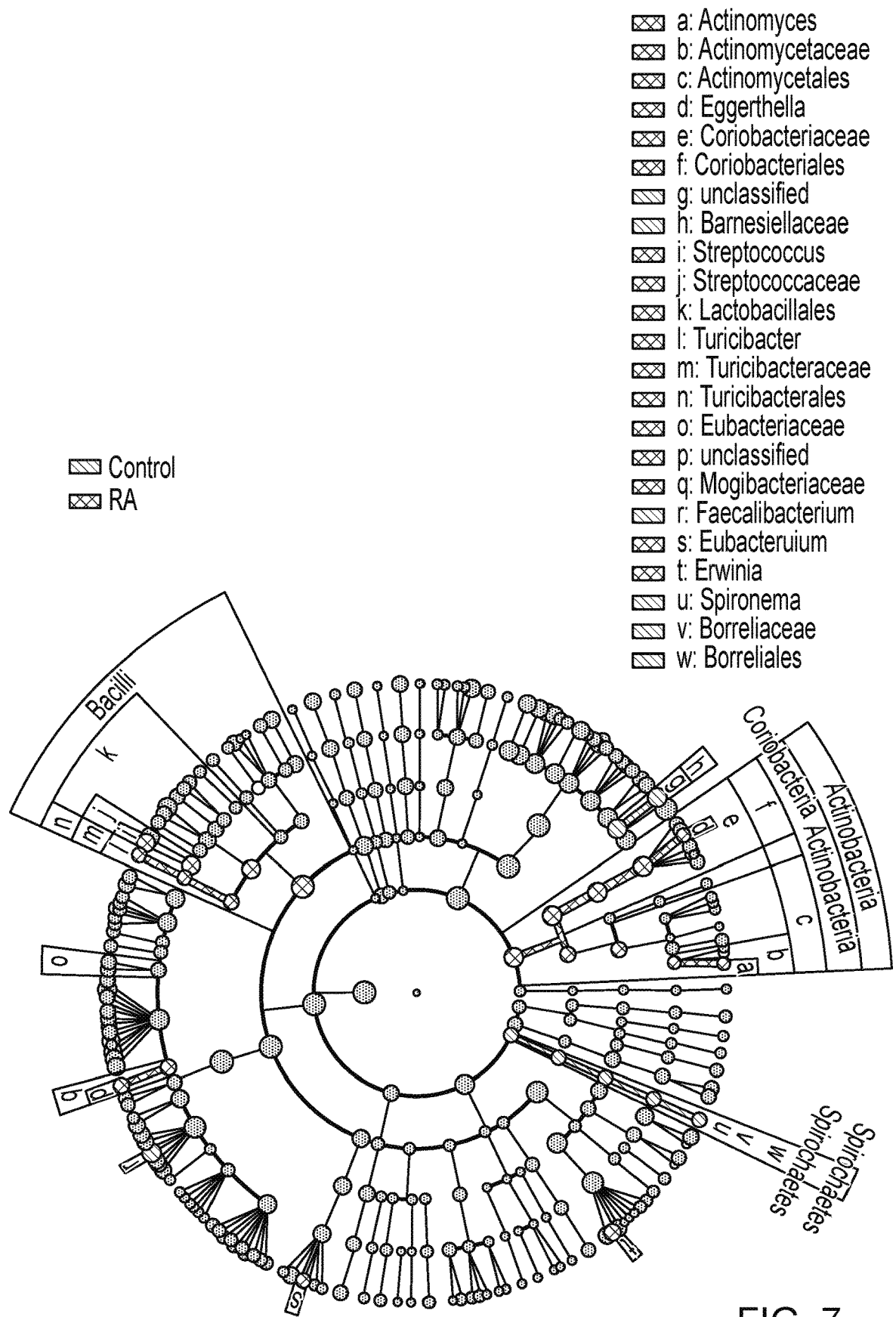
FIG. 7. Patients with RA were characterized by expansion of *Eggerthella* and other rare lineage. LefSe analysis was performed with a less stringent p value cutoff of 0.05 to identify generally present with low abundance in healthy controls. (top, left) The taxa identified by LEfse analysis are highlighted on the phylogenetic tree, and (top, right) their LDA score are shown. Among all these identified taxa, the association of genus *Eggerthella* is the most significant even after Bonferroni correction was used for multiple testing corrections. The genus *Faecalibacterium* had the largest LDA score. The bottom, left and right panels are representations of abundance of *Eggerthella, Collinsella*, and *Faecalibacterium* in RA patients, first degree relatives, and healthy controls.
Figure 7:
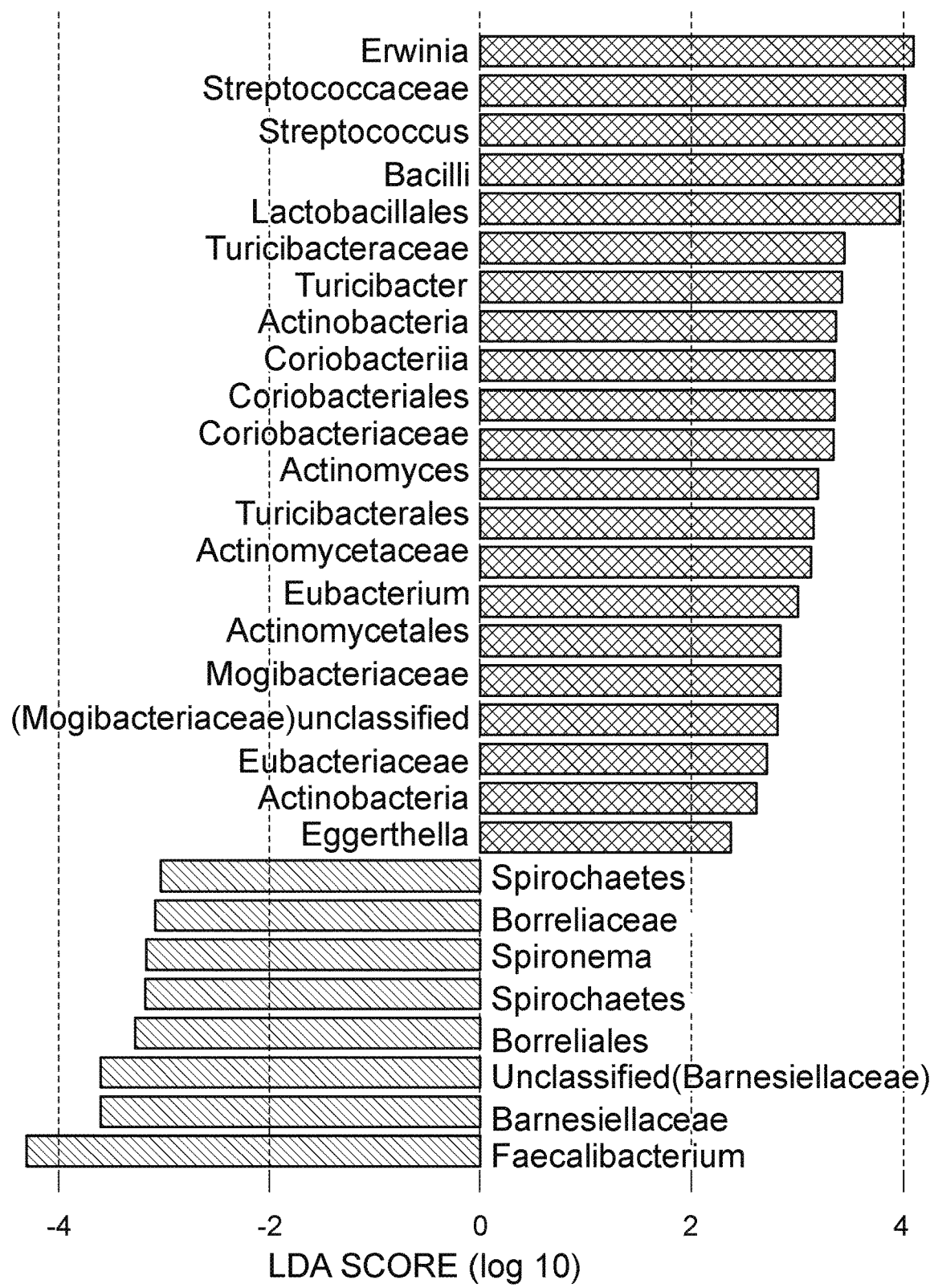
Figure 7:
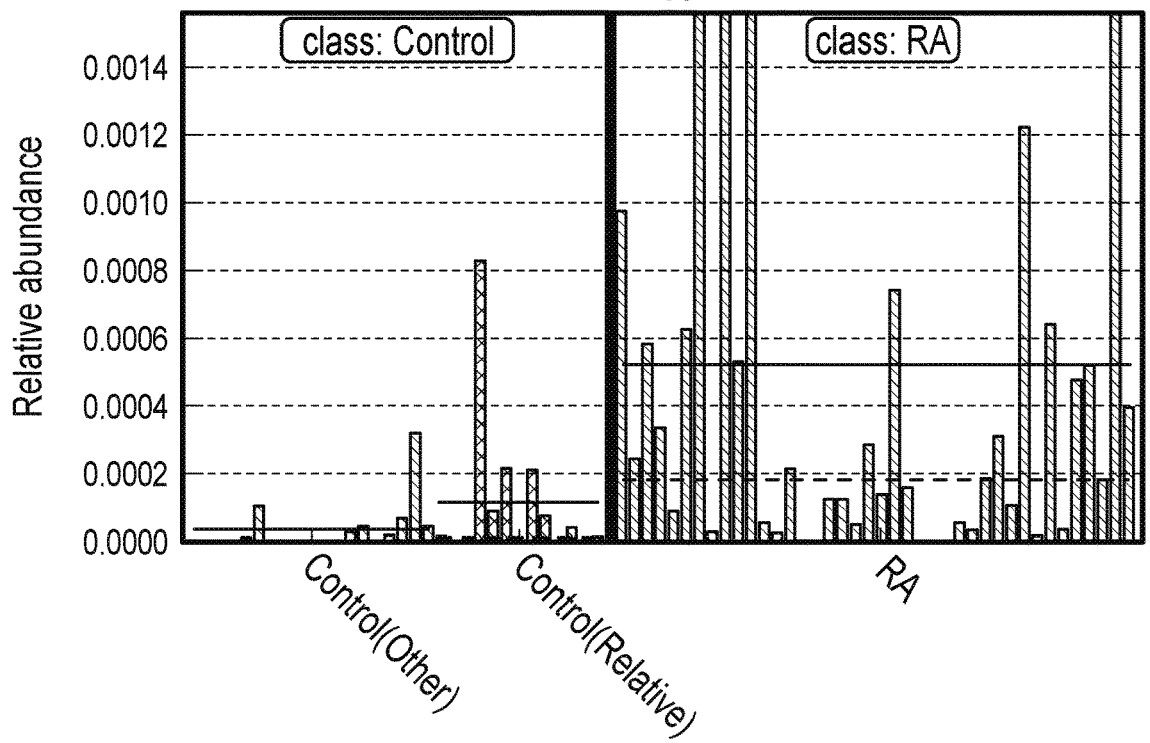
Figure 7:
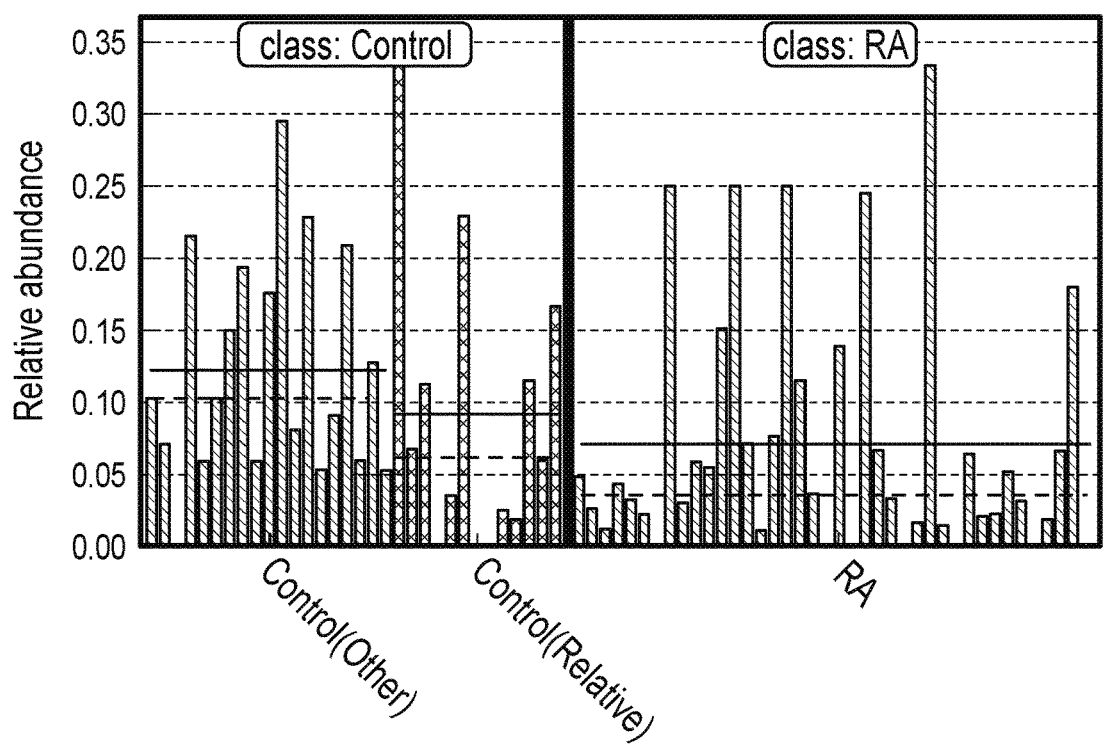
Figure 7:
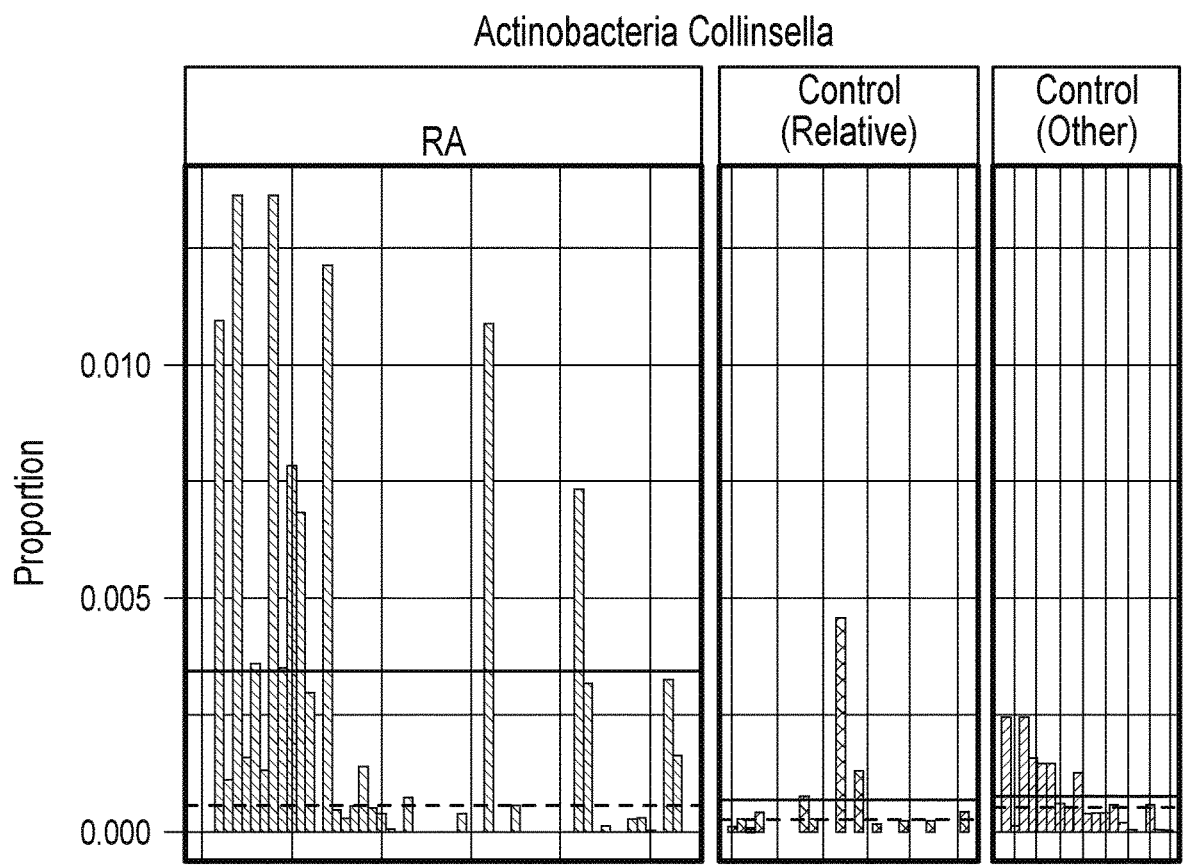
Figure 11:
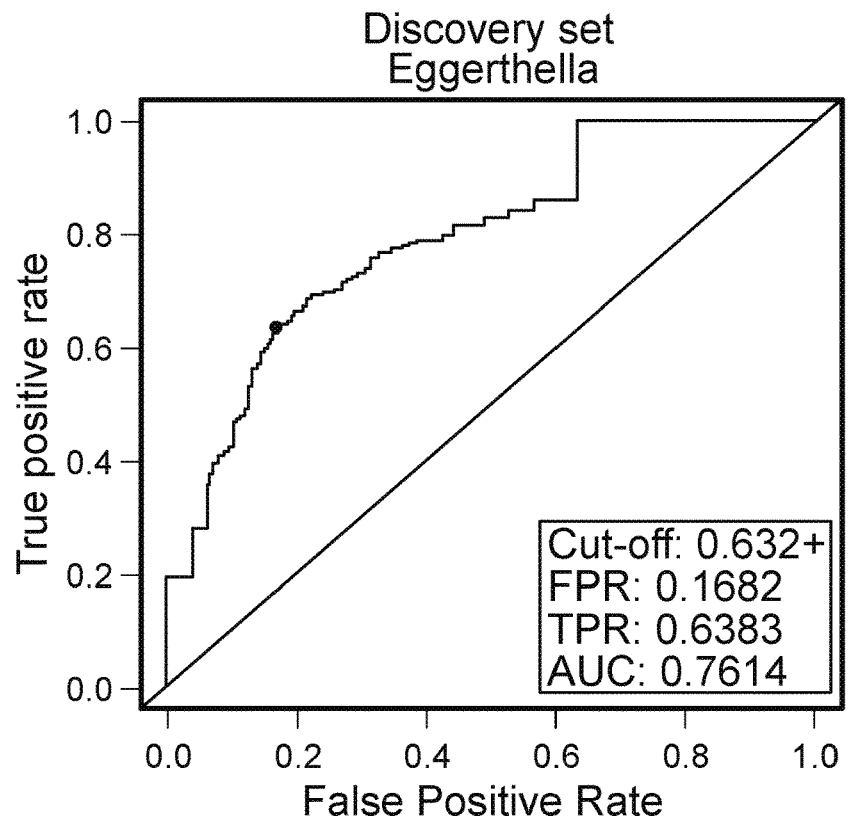
FIG. 11. The genus *Eggerthella* demonstrated the most significant association with RA (N=40), which remained significant even after conservative Bonferroni correction for multiple testing was applied (P=1.4e-5) (Discovery set). The association of *Eggerthella* with RA was confirmed in a larger set of N=60 patients.
Figure 11:
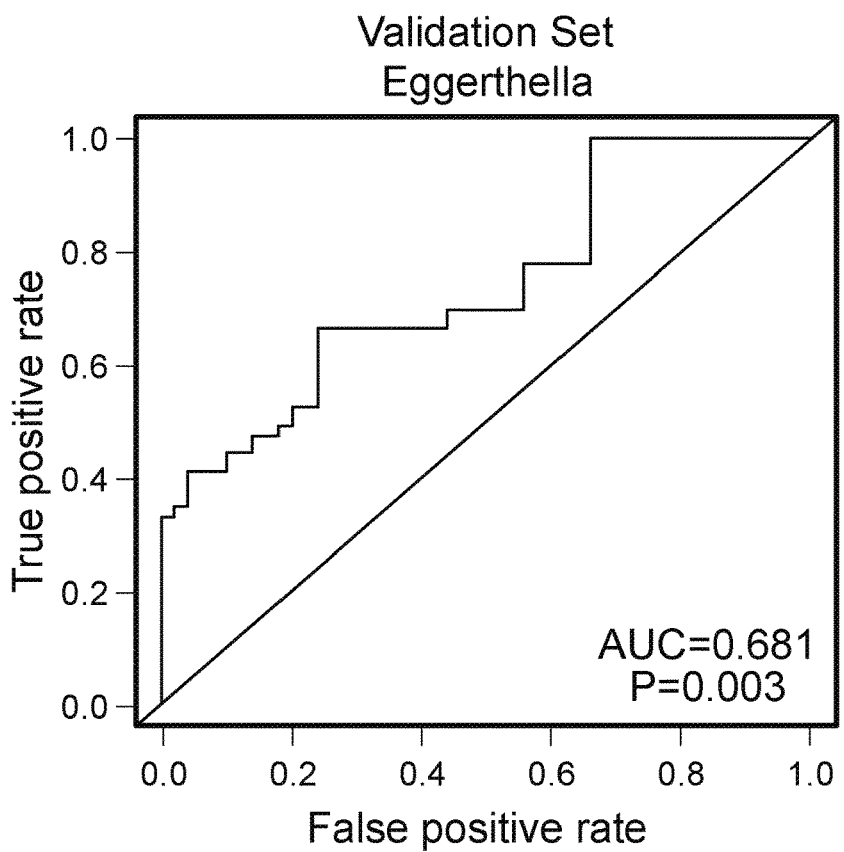

Among all these identified taxa, the association of genus *Eggerthella* exhibited the most significant association with RA (FIG. 11). After Bonferroni correction for multiple test correction, the most significant difference was observed in the abundance of *Eggerthella* in RA patients compared to controls (q=0.0009). This association also was tested by performing LFfSe analysis with a less stringent p value cutoff of 0.05 (FIG. 7, top panels). The cladogram reveals the distance between bacterial clades in patients and controls (FIG. 7, top left). The taxa with high LOD scores in controls and patients are depicted in FIG. 7, top right. Among the common taxa, *Faecalibacterium* exhibited the highest LOD score for low abundance, while *Erwinia* exhibited higher abundance in RA patients than controls (FIG. 7, lower panels). Relative abundance of *Eggerthella*, *Collinsella*, and *Faecalibacterium* in patients, controls, and relatives (FIG. 7, lower panels) exhibited a significant difference in RA patients and controls and confirmed the above observations.

TABLE 3

RA patients exhibited expansion of *Eggerthella lenta*.

| | p value | q value | Fold change | LDA score |
|---|---|---|---|---|
| Actinobacteria | 0.003 | 0.02 | 4.5 | 3.4 |
| Actinobacteria; Coriobacteriaceae | 0.005 | 0.09 | 4.5 | 3.4 |
| Actinobacteria; *Eggerthella* | 1.4E−05 | 0.0009 | 7.9 | 2.4 |
| Bacteroidetes; Barnesiellaceae | 0.019 | 0.12 | 0.63 | 3.6 |
| Firmicutes; Turicibacteraceae | 0.020 | 0.12 | 4.0 | 3.5 |
| Firmicutes; Eubacteriaceae | 0.017 | 0.12 | 8.0 | 2.7 |
| Firmicutes; Mogibacteriaceae | 0.028 | 0.15 | 2.2 | 2.8 |
| Firmicutes; Streptococcaceae | 0.033 | 0.15 | 3.2 | 4.0 |
| Firmicutes; Turicibacteraceae | 0.020 | 0.12 | 4.0 | 3.4 |
| Spirochaetes | 0.018 | 0.07 | 0.10 | 3.0 |
| Spirochaetes; Borreliaceae | 0.018 | 0.12 | 0.10 | 3.1 |

Figure 8A:
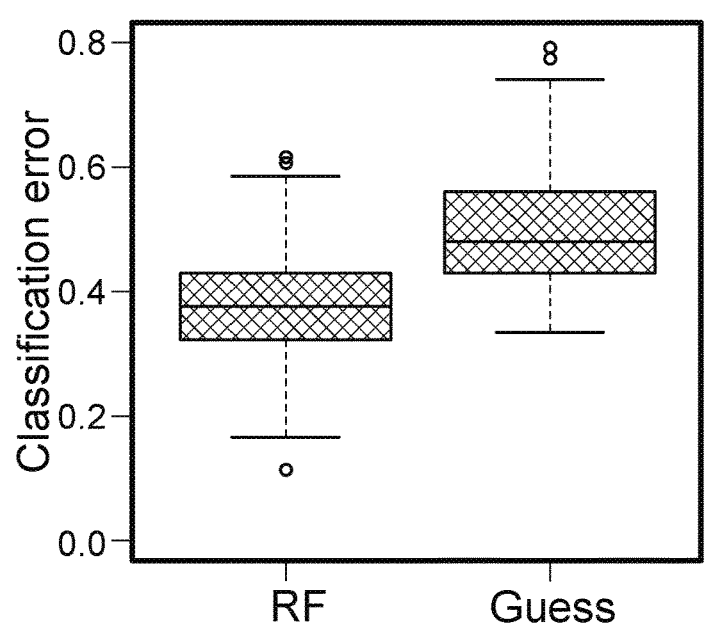
FIGS. 8A-C. Prediction model for RA by machine learning using Random Forest. Random Forest (RF) algorithm, an ensemble classifier built upon many decision trees, was used to build a prediction model. The input of the RF classifier was the genus-level abundance data, and the output was the predicted class label (RA' and 'Control'). (A) The Boruta variable selection algorithm. (B) Using Boruta feature selection, three confirmed genera: *Eggerthella, Faecalibacterium* and *Collinsella*, and two suggested genera: *Rikenella* and *Lachnobacterium* provided a predictive profile. (C) Hierarchical clustering based on the abundance profile of these five genera revealed that the RA samples are generally clustered together.

Expansion of Rare Taxa with Decrease in Abundance of Common Taxa Characterize RA Univariate tests for marginal association of microbial taxa with the disease state may not be powerful to identify taxa that are individually weak but jointly strong predictor of the disease state. The loss of power of marginal test could be due to multiple testing corrections, increased variability of the un-modeled part, and inability of modeling interactions between taxa. To identify the taxa that are jointly strong predictor of the disease state, machine learning Random Forest (RF) algorithm, an ensemble classifier built upon many decision trees, was used to build a prediction model. This Joint analysis method can potentially have a better power to identify relevant taxa and offer extra insight of disease pathogenicity. Genus-level abundance was used to predict the bacterial clades classified for RA and controls. The Boruta variable selection algorithm produced an importance value for each genus based on the loss of classification accuracy by the random permutation of the abundance profile of the genus. To have an unbiased assessment of the RF classification error, bootstrap sample was used to train the RF classifier and predict the class label on the unused sample. Based on 500 bootstrap samples, a mean classification error of 0.38, compared to 0.47 based on random guess, was achieved. The results indicated that RA samples differ in genus-level abundance from the control samples (p<2.2E-16, Friedman Rank Sum test, FIG. 8A). The observations from random forest agreed with the single-taxon based test (Table 4).

Figure 8B:
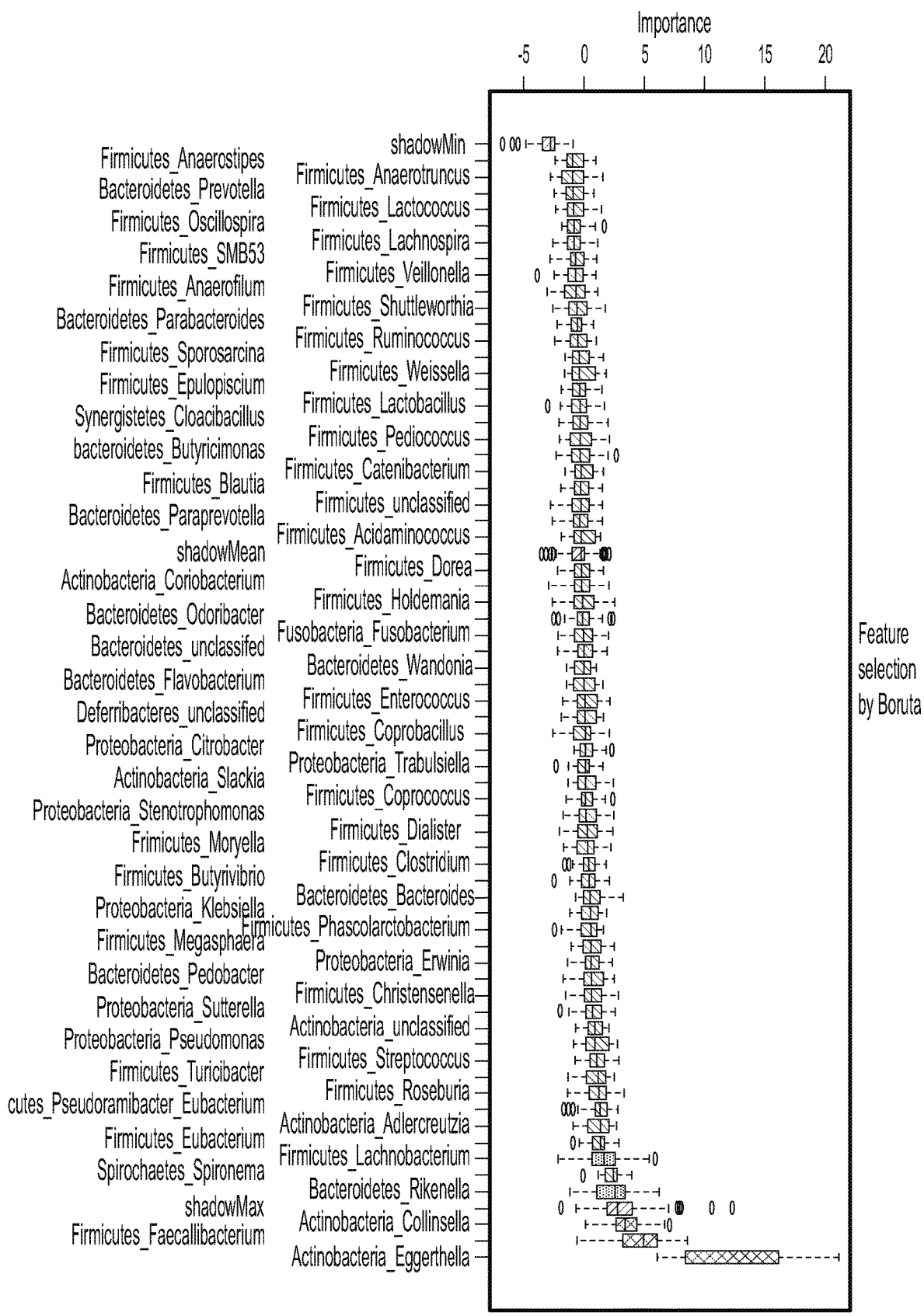

To determine the statistical significance of the observed importance measures, the Boruta feature selection method, which compared the observed importance measures to the importance measures produced under permuted taxa, was applied. Using Boruta feature selection, three confirmed genera (*Eggerthella*, *Faecalibacterium* and *Collinsella*) and two suggested genera (*Rikenella* and *Lachnobacterium*) were selected (FIG. 8B).

Figure 8C:
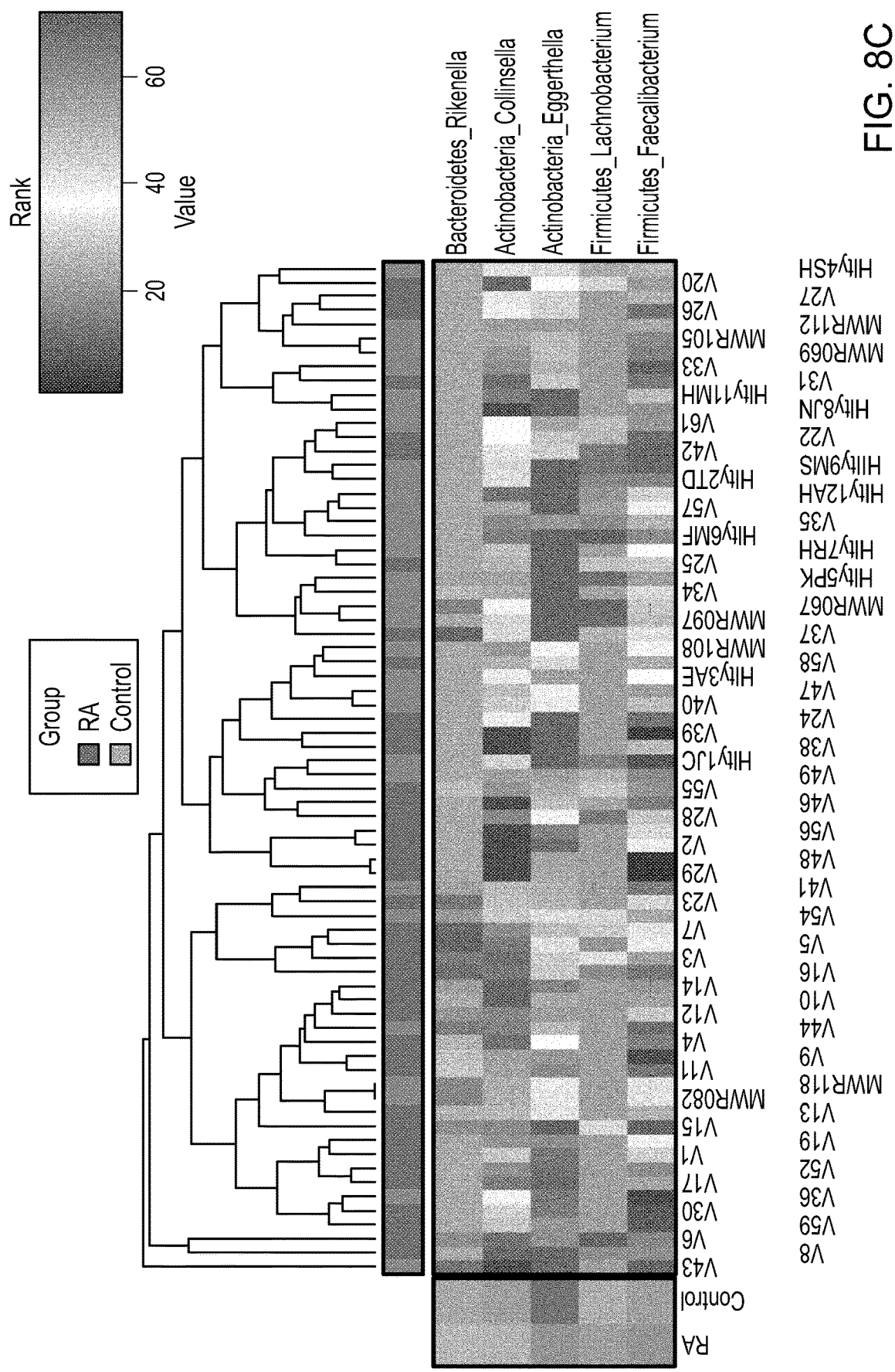

While single taxon tests confirmed the differences in abundance of *Faecalibacterium* and *Eggerthella* in RA patients as compared to controls ((p=1.4e-05 and 0.02), the abundance of *Collinsella* was not observed, suggesting a potential power of combined analysis of the data. The abundance of *Collinsella* was higher in RA patients compared to controls (FIG. 8C). Hierarchical clustering based on the abundance profile of the three confirmed genera revealed that the samples from RA patients generally clustered together (FIG. 8D).

TABLE 4

|  | MeanDecreaseGini | MeanDecreaseAccuracy |
| --- | --- | --- |
| Actinobacteria_Eggerthella | 3.343755 | 0.031613 |
| Firmicutes_Faecalibacterium | 1.509349 | 0.003339 |
| Actinobacteria_Collinsella | 1.139226 | 0.005387 |
| Firmicutes_Streptococcus | 1.031677 | 0.004444 |
| Firmicutes_Eubacterium | 1.030072 | 0.005289 |
| Firmicutes_Turicibacter | 0.983044 | 0.003373 |
| Actinobacteria_Adlercreutzia | 0.910195 | 0.004182 |
| Firmicutes_Moryella | 0.908651 | 0.000697 |
| Proteobacteria_Erwinia | 0.876164 | 0.001355 |
| Firmicutes_Clostridium | 0.830134 | 9.75E−05 |
| Firmicutes_Roseburia | 0.821583 | 0.003173 |
| Firmicutes_Ruminococcus | 0.769776 | 0.0004 |
| Firmicutes_unclassified | 0.76454 | 0.000901 |
| Proteobacteria_Sutterella | 0.753107 | 0.003043 |
| Firmicutes_Coprococcus | 0.714581 | 0.001902 |
| Bacteroidetes_unclassified | 0.696532 | −9.56E−05 |
| Firmicutes_Phascolarctobacterium | 0.638495 | −0.00016 |
| Firmicutes_Oscillospira | 0.616102 | 1.51E−05 |
| Firmicutes_Enterococcus | 0.603106 | 0.000121 |
| Bacteroidetes_Bacteroides | 0.592061 | 0.00224 |
| Firmicutes_Anaerotruncus | 0.548713 | −0.00069 |
| Firmicutes_Holdemania | 0.535563 | 0.000493 |
| Firmicutes_Dialister | 0.524454 | 0.00185 |
| Firmicutes_Dorea | 0.515209 | −0.00078 |
| Bacteroidetes_Odoribacter | 0.508344 | 0.001012 |
| Bacteroidetes_Parabacteroides | 0.500659 | 0.000614 |
| Firmicutes_Christensenella | 0.498419 | 0.001141 |
| Firmicutes_Coprobacillus | 0.492294 | −0.00105 |
| Proteobacteria_Klebsiella | 0.48442 | 0.000922 |
| Firmicutes_Lachnospira | 0.479818 | −0.00136 |
| Firmicutes_Lactobacillus | 0.474225 | −0.00104 |
| Actinobacteria_unclassified | 0.471309 | 0.001054 |
| Proteobacteria_Pseudomonas | 0.467857 | 0.003838 |
| Firmicutes_Pseudoramibacter_Eubacterium | 0.459554 | 0.001924 |
| Firmicutes_Anaerofilum | 0.44783 | −0.00208 |
| Spirochaetes_Spironema | 0.4451 | 0.002226 |
| Firmicutes_Lactococcus | 0.44262 | −0.00017 |
| Firmicutes_Blautia | 0.440753 | −0.00095 |
| Firmicutes_Butyrivibrio | 0.428609 | 0.000753 |
| Bacteroidetes_Flavobacterium | 0.405337 | 0.000289 |
| Firmicutes_Veillonella | 0.395236 | −0.00158 |
| Firmicutes_Lachnobacterium | 0.390891 | 0.00137 |
| Bacteroidetes_Butyricimonas | 0.376701 | 0.000318 |
| Firmicutes_Anaerostipes | 0.373949 | −0.00066 |
| Bacteroidetes_Prevotella | 0.359883 | 0.000619 |
| Firmicutes_Shuttleworthia | 0.350173 | −0.00035 |
| Firmicutes_SMB53 | 0.341791 | −0.0005 |
| Firmicutes_Epulopiscium | 0.341154 | −0.00099 |
| Bacteroidetes_Rikenella | 0.337038 | 0.001548 |
| Firmicutes_Megasphaera | 0.307556 | 0.000232 |
| Proteobacteria_Trabulsiella | 0.285348 | −0.00015 |
| Actinobacteria_Coriobacterium | 0.284408 | −0.00051 |
| Proteobacteria_Citrobacter | 0.27412 | 0.00017 |
| Bacteroidetes_Pedobacter | 0.274077 | 0.000904 |
| Proteobacteria_Stenotrophomonas | 0.271392 | 0.001156 |
| Firmicutes_Catenibacterium | 0.243844 | 0.000498 |
| Bacteroidetes_Paraprevotella | 0.232607 | −3.98E−05 |
| Fusobacteria_Fusobacterium | 0.184539 | 0.000363 |
| Firmicutes_Acidaminococcus | 0.164159 | −0.00021 |
| Firmicutes_Weissella | 0.139408 | −9.03E−05 |
| Deferribacteres_unclassified | 0.133677 | −0.0009 |
| Firmicutes_Pediococcus | 0.110149 | 0.000301 |
| Actinobacteria_Slackia | 0.109051 | 0.00034 |
| Synergistetes_Cloacibacillus | 0.08936 | 0.000292 |
| Firmicutes_Sporosarcina | 0.053301 | 0.00024 |
| Bacteroidetes_Wandonia | 0.028508 | 8.00E−05 |

Figure 5:
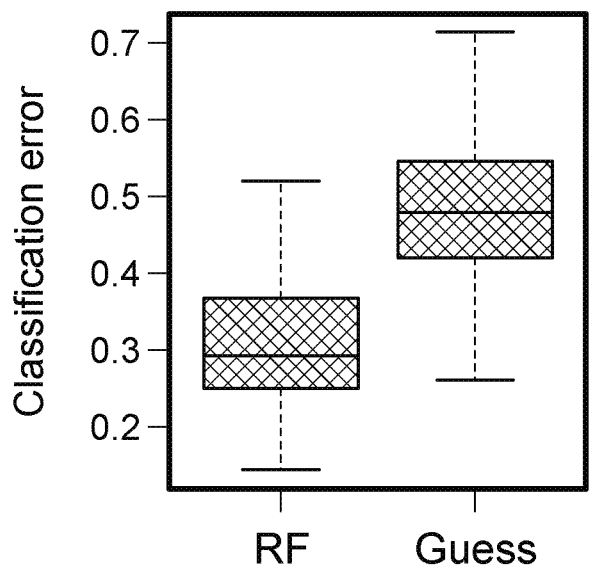
FIG. 5. Prediction model of RA status based on OTU-level data and Random Forest (RF). (Top, left) Classification error of RF compared to random guess, which is based on the label of the majority class in the training data. The classification error was assessed based on 500 bootstrap samples. (Top, right) The normalized importance values for all the OTUs produced by Borunta feature selection algorithm. Confirmed OTUs are highlighted in green, while suggested OTUs are in yellow. (Bottom) Hierarchical clustering based on the abundance profile of the confirmed/suggested taxa show that the RA samples are generally clustered together.
Figure 5:
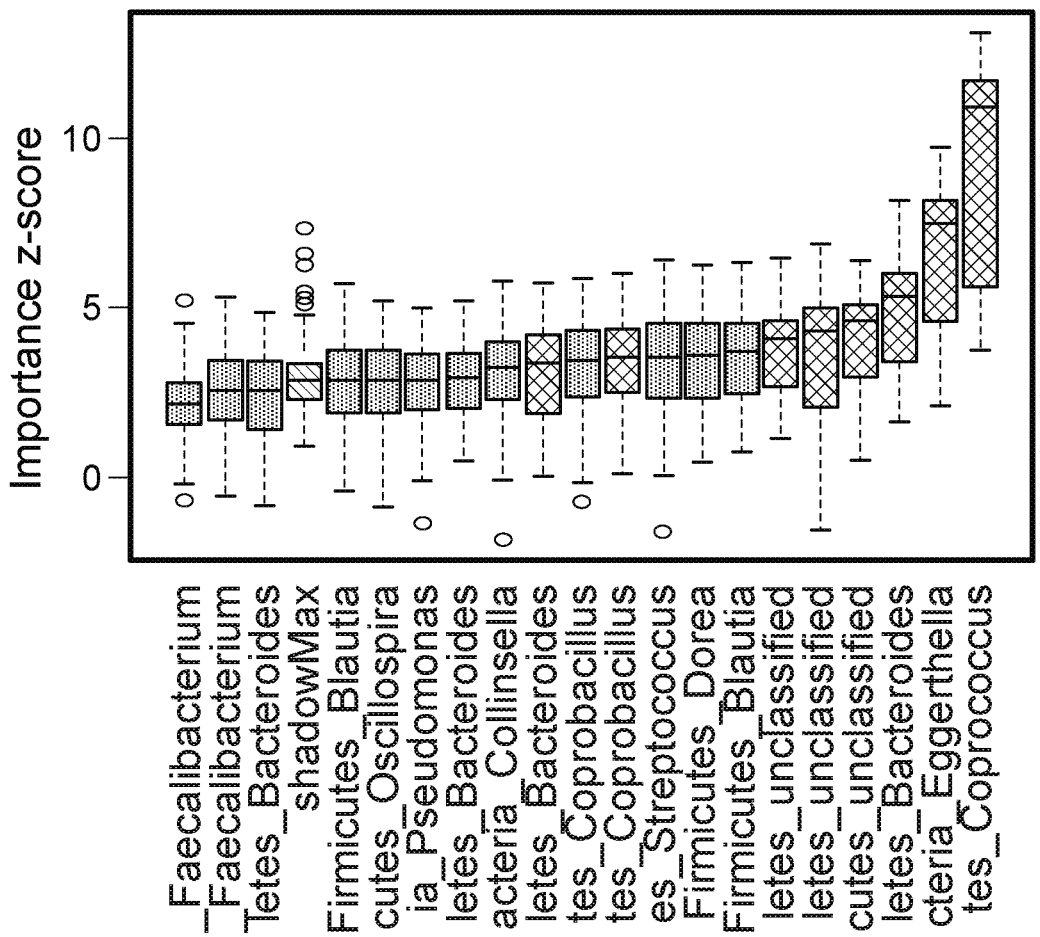
Figure 5:
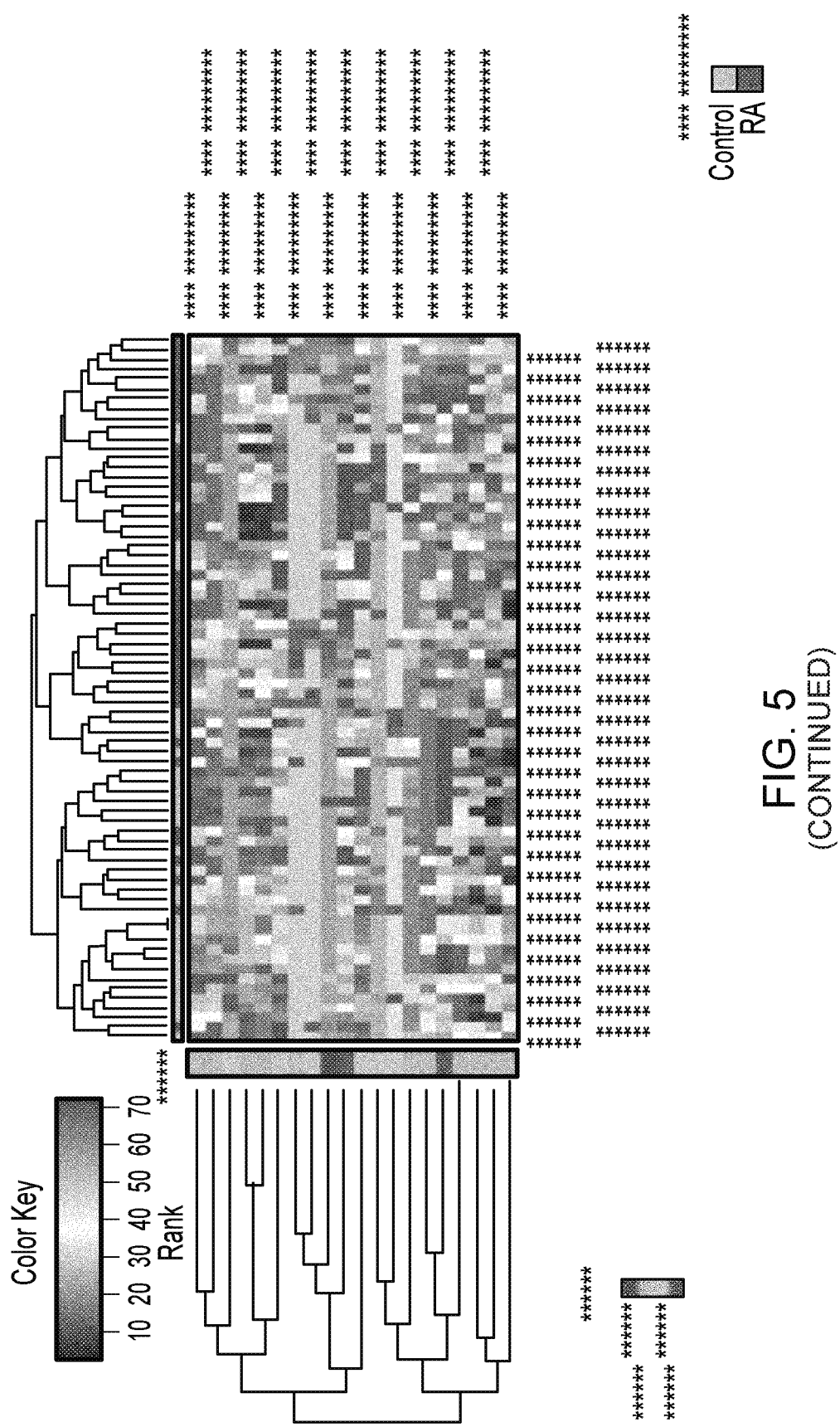

To specifically pinpoint a species that can predict risk for RA, Randon Forest based on the OTUs was conducted. This led to an even lower classification error of 0.30 (FIG. 5). Many OTUs from genus *Eggerthella, Collinsella* and *Faecalibacterium* were represented in the OTUs selected by the Boruta feature. Overall these observations demonstrated that while the community structure between RA patients and controls is similar in the presence of the abundant taxa except *Faecalibacterium*, they differ in the presence of rare represented genera.

Metabolome is Associated with Microbiome in RA

Figure 9:
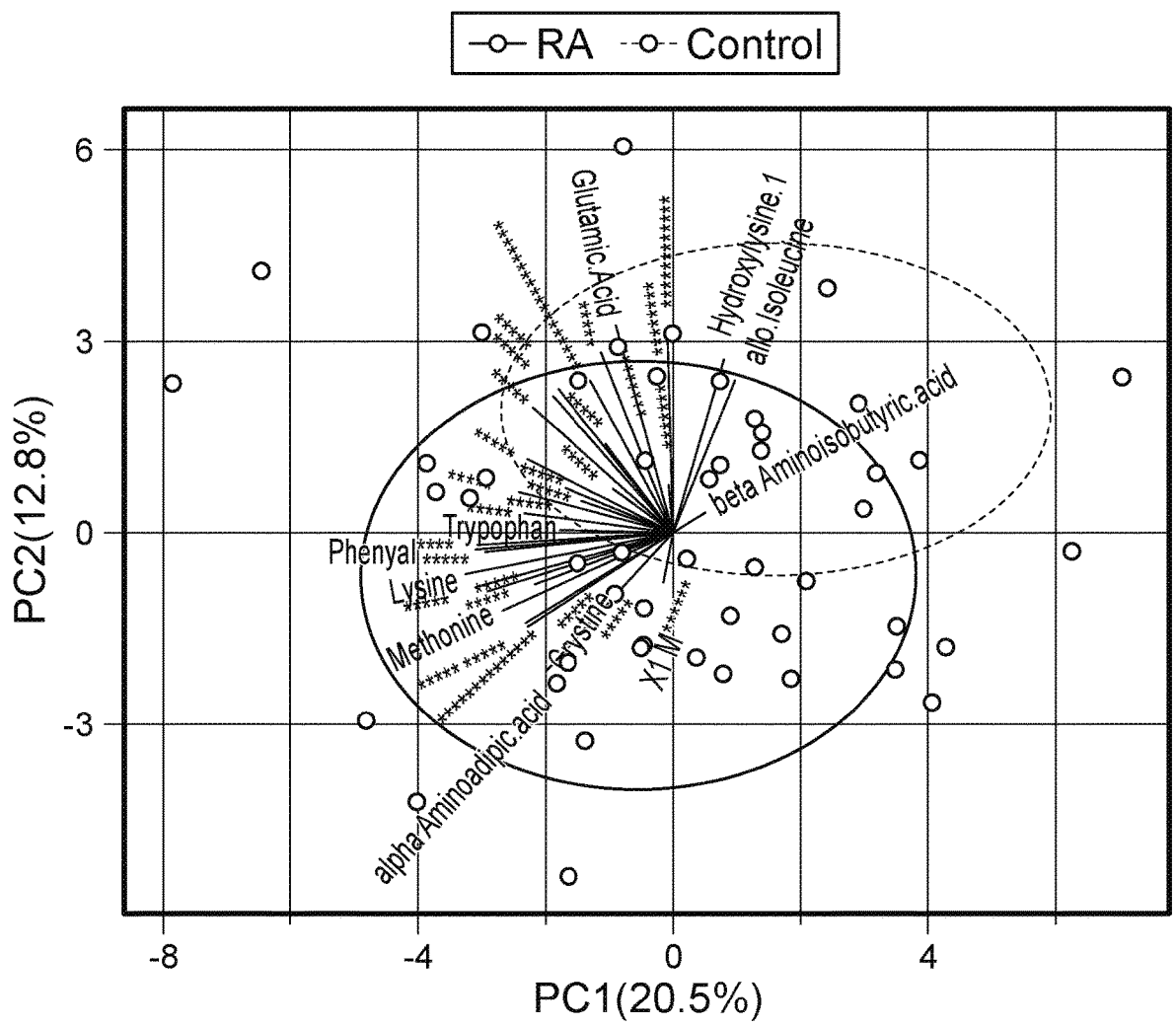
FIG. 9. Association of metabolite levels in plasma with RA disease status and gut microbiota. (top) PCA reveals the overall metabolite profile is different between the RA patients and their relatives. (middle) Differential abundant metabolites between RA patients and their relatives at a false discovery rate of 0.05. (bottom) The Spearman rank correlation between the abundance of the three genera *Collinsella, Eggerthella*, and *Facealibacterium* and metabolites (**p<0.01, *p<0.05, .p<0.1). The differential abundant metabolites show strong correlation with the abundance of *Collinsella*.
Figure 9:
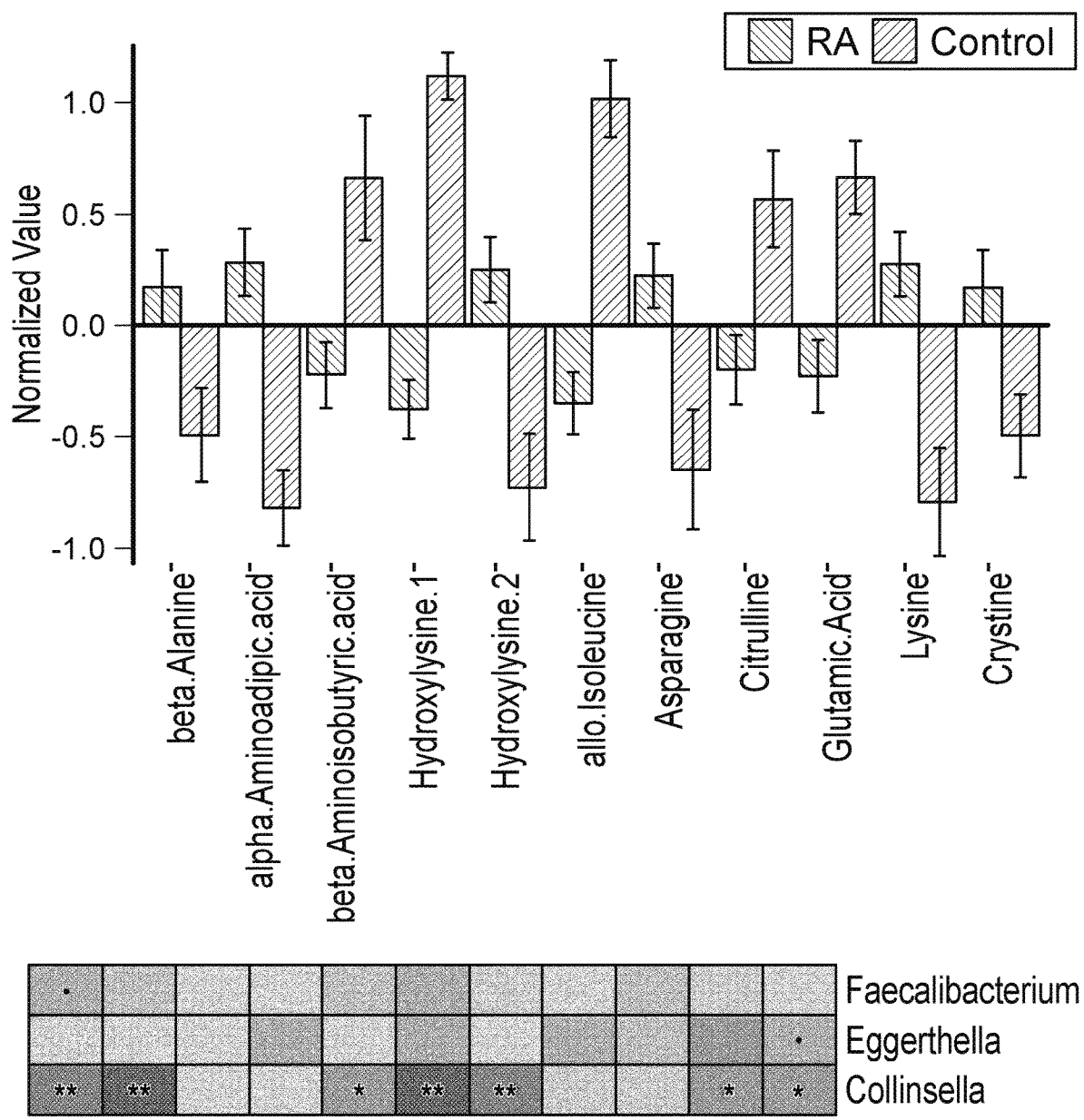
Figure 15:
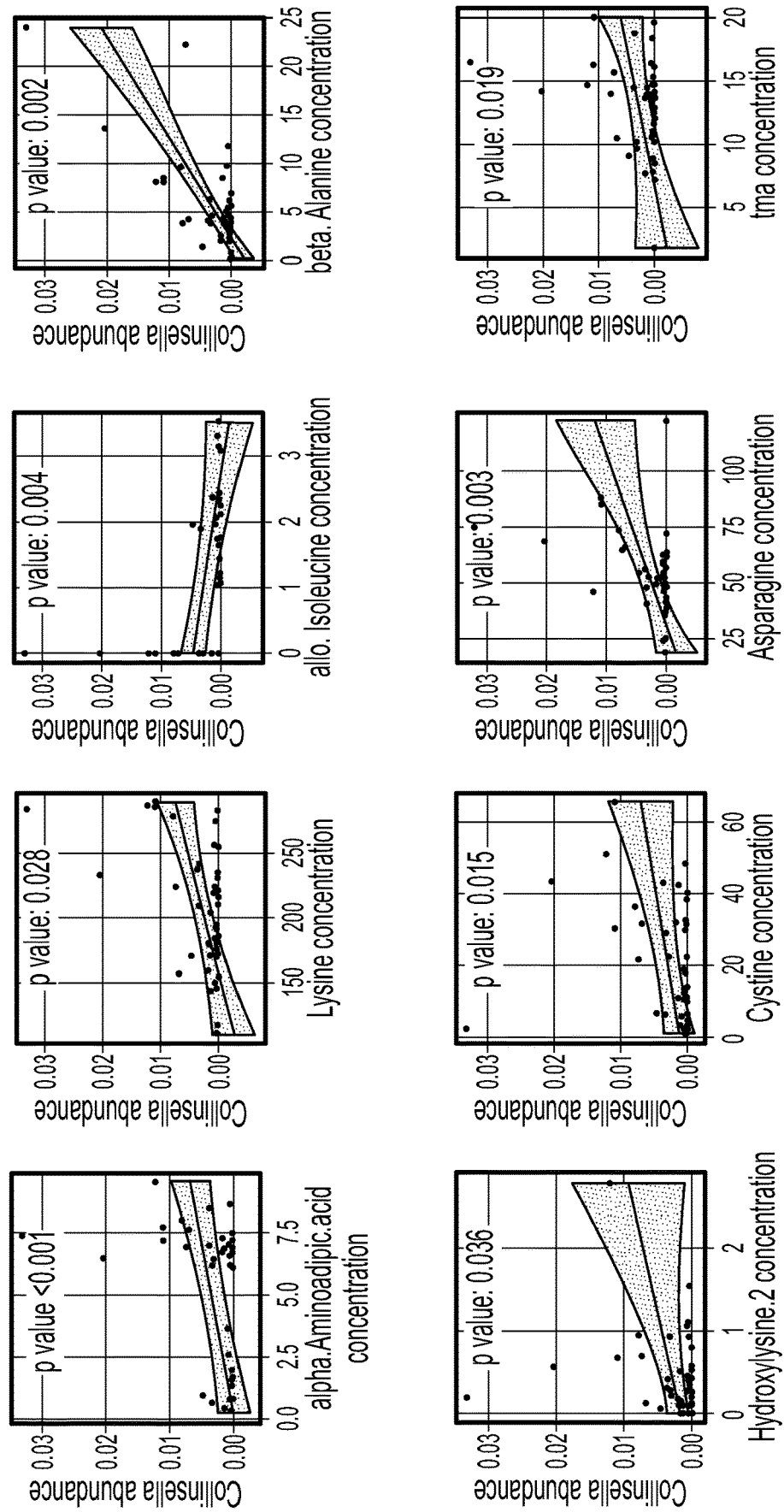
FIG. 15. Scatterplots showing the correlation of the abundance of differentially abundant metabolite with *Collinsella* abundance. Significance was assessed by Spearman rank correlation test. The line shows the fitted linear regression line with the gray area indicating the 95% confidence band.

The blood levels of 44 metabolites were measured in both RA patients and their relatives (N=51). The overall metabolomic profiles differed significantly between RA subjects and their relative (FIG. 9, top; p<0.001, PERMANOVA based on Euclidean distance of the metabolite levels). Interestingly, no gender differences were observed. Eleven metabolites were observed to occur with significant difference between patients and first degree relatives (two-sample t tests at an FDR of 0.05; FIG. 9, middle), of which six metabolites had higher levels in the RA patients. Correlation between the microbiota and the overall metabolomic profile revealed a significant association between the metabolome PC1 and the microbiota within the RA patients (PERMANOVA, p=0.03, generalized UniFrac distance). Associations between the 11 differential metabolites and the 3 differential abundant genera (*Collinsella, Eggerthella*, and Facealibacterium) were tested using Spearman's rank correlation test. The abundance of *Collinsella* correlated strongly with higher levels of 3 metabolites, while alloisoleucine showed an inverse relation with abundance of *Collinsella* (FIG. 9, bottom; and FIG. 15).

Figure 16A:
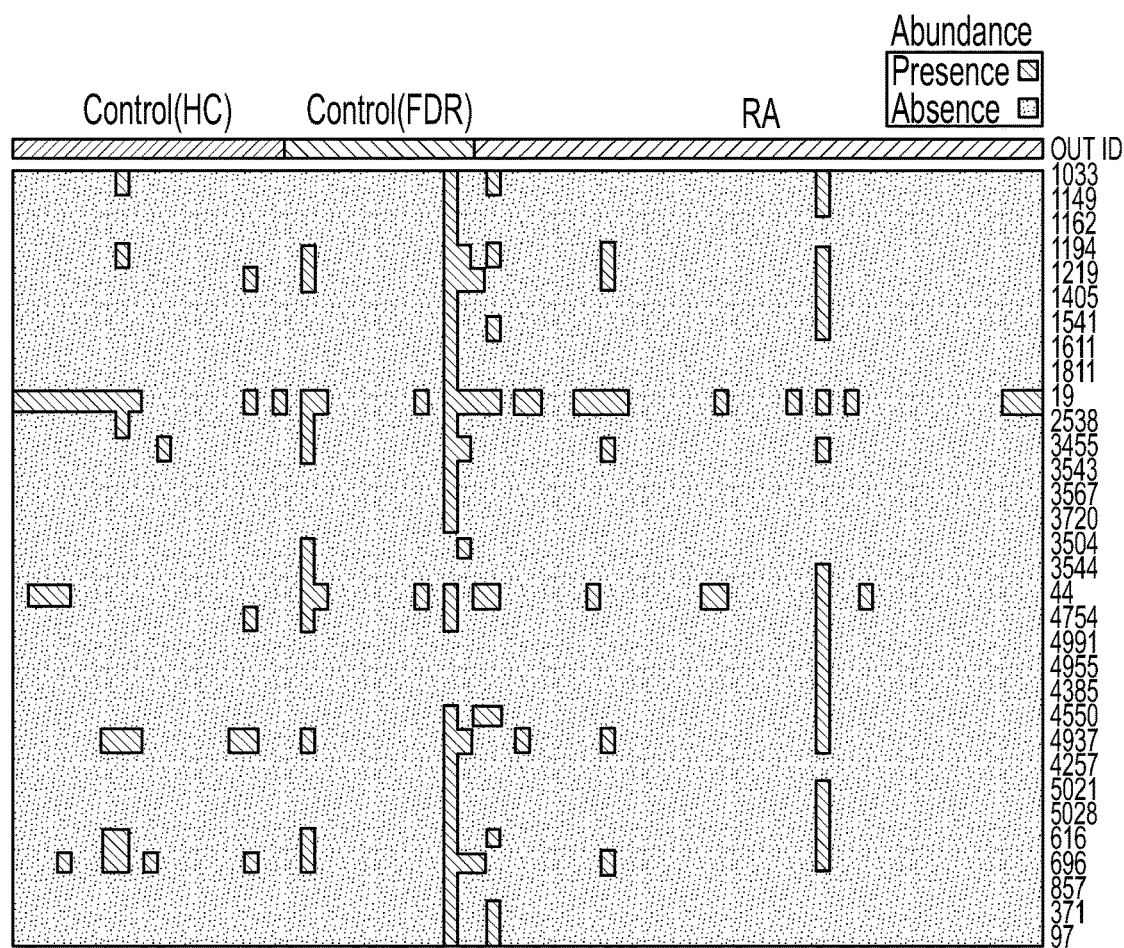
FIGS. 16A-C. The relative abundance of *Prevotella Copri* (*P. Copri*) does not show significant difference between RA and controls. (A) The presence of *P. Copri* OTUs is similar between RA and controls. The row names of the heatmap are IDs of these *P. Copri* OTUs. Column names are sample IDs. Dark and light shading indicate presence and absence of the OTUs, respectively. (B) The relative abundance of the *P. Copri* OTUs does not increase in RA patients. (C) The relative abundance of the *P. Copri* OTUs in RA patients does not differ according to the HLADR4 status.
Figure 16B:
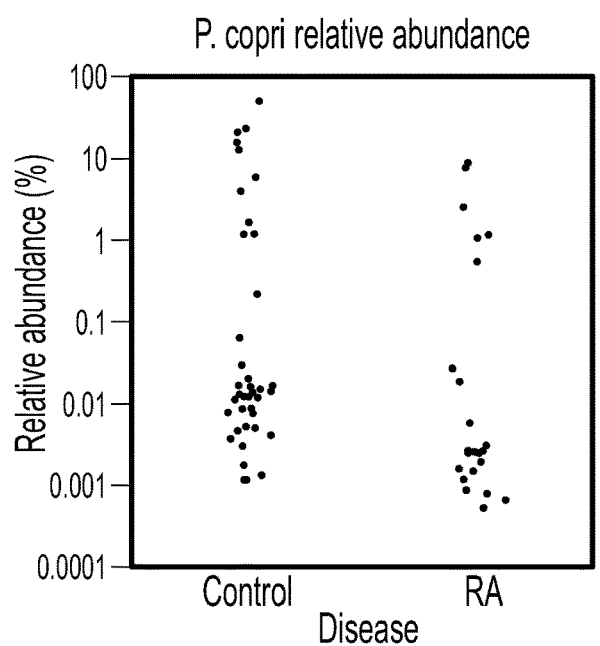
Figure 16C:
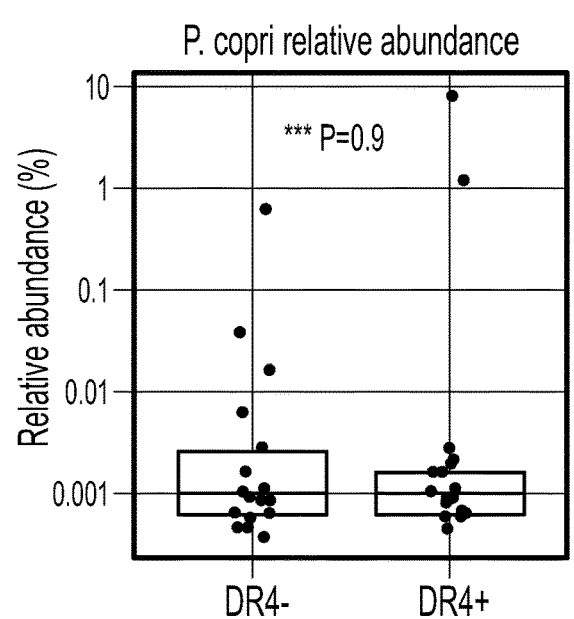

The potential association of *Prevotella copri* with new-onset untreated RA (Scher et al., *Elife*, 2:e01202 (2013)) was investigated. No significant enrichment of *P. copri* OTUs was observed in patients with RA. Moreover, the relative abundance of *P. copri* OTUs was similar between patients and non-RA controls (FIGS. 16A and 16B). Also, there was no difference in the presence of *P. copri* in DR4 positive compared to DR4 negative patients (FIG. 16C).

Figure 13:
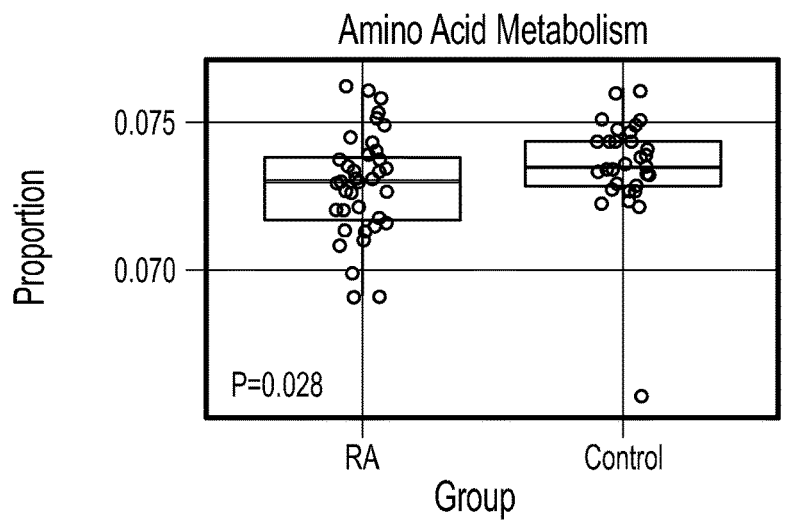
FIG. 13. RA gut microbiota has decreased function in amino acid metabolism. The abundance of the KEGG pathway categories was calculated based on PICRUSt. The three horizontal lines of the box represents the first, second (median) and third quartile respectively with the whisk extending to 1.5 inter-quartile range (IQR).

PICRUSt was applied to infer the functional content of the microbiota based on closed-reference OTU picking. Among 26 KEGG pathways tested, the amino acid metabolism pathway exhibited differences between RA patients and non-RA controls. Specifically, a decrease in OTUs with amino acid metabolism capabilities was measured in patients with RA compared to non-RA controls (unadjusted P=0.03, FIG. 13).

*Collinsella* Enhances Disease Severity in Humanized Mice

Figure 10A:
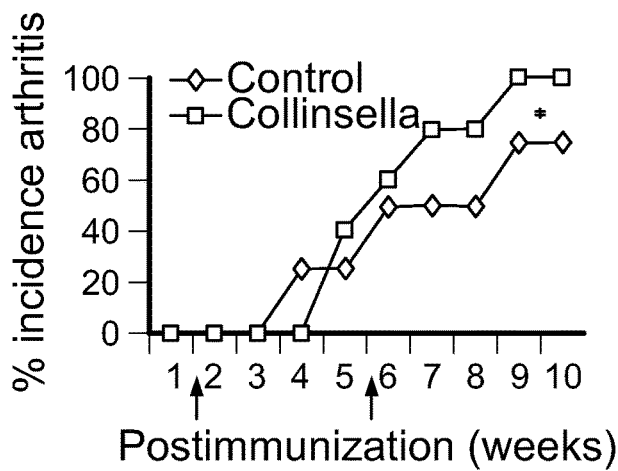
FIGS. 10A-E. HLA-DQ8 mice were immunized with type II collagen (CII) to induce arthritis and not-treated (Control, N=8) or treated with *Collinsella aerofaciens* (N=10) two weeks post-immunization every alternate day for four weeks (marked with arrows). Mice were followed for (A) incidence and onset of arthritis and (B) disease severity. *Collinsella* enhances T cell proliferation. (C) T cell proliferation was measured by culturing FAC sorted CD4 cells from spleens of CII-primed mice cultured with CII and dendritic cells that were pre-cultured with *Collinsella* or supernatants (sup) of *Collinsella* cultures for 4 hours. *P<0.001. *Collinsella* reduces the expression of tight junction protein Zo-1. (D) CACO-2 cells cultured with or without *Collinsella* or supernatants (sup) of *Collinsella* culture stained with Zo-1 (arrow). (E) Mean fluorescence intensity of Zo-1 expression in CACO-2 cells alone and in the presence of *Collinsella aerofaciens* exhibited reduced expression of Zo-1 in the later.
Figure 10B:
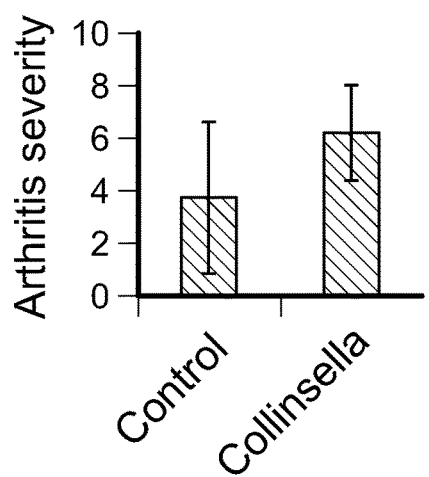
Figure 10C:
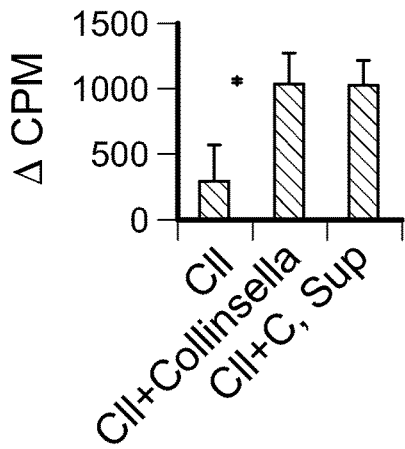

CIA-susceptible HLA-DQ8 mice were treated or not with *Collinsella aerofaciens*. To simulate arthritic condition, mice were orally gavaged with *Collinsella* two weeks after inducing arthritis, and progression of arthritis was monitored. Treated mice developed arthritis with increased incidence and severity compared to non-treated mice (100% incidence in treated vs 75% in untreated, P<0.05) although disease severity was not statistically significantly increased (FIGS. 10A and B). To determine the influence of *Collinsella* on immune response, proliferation of CD4 cells sorted from spleen of CII-primed DQ8 mice to CII when cultured with DCs was tested. The DCs were pre-cultured in vitro with *Collinsella* as well as with supernatants of *Collinsella*. CD4 T cells generated a significantly robust response to CII when DCs were precultured with the bacteria as compared to untreated DCs (P<0.02). DCs sensitized to supernatants of *Collinsella* culture also exhibited a higher response than controls although the difference did not reach significance (FIG. 10C, P<0.08).

Figure 10D:
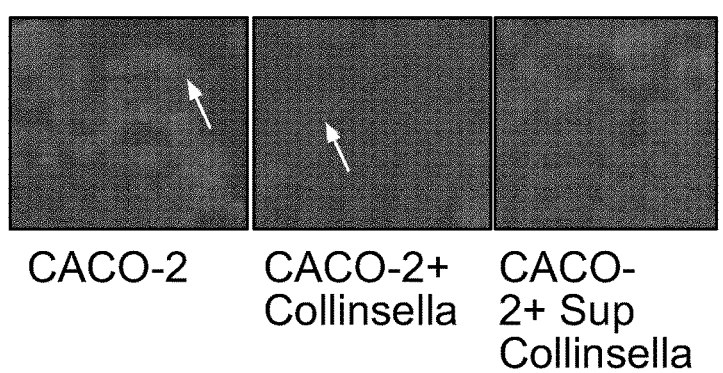
Figure 10E:
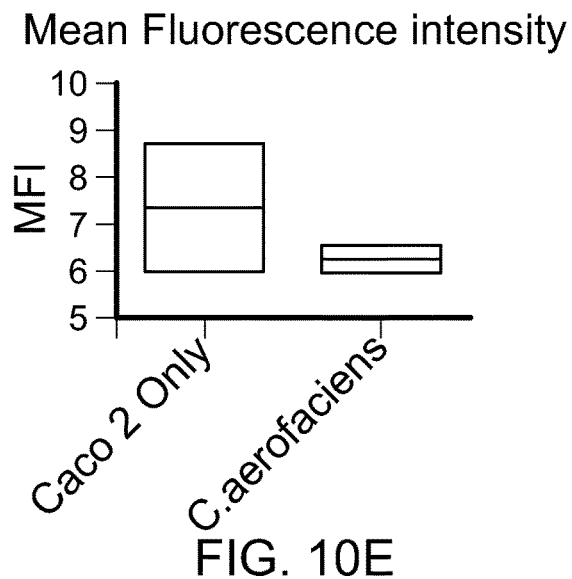
Figure 17A:
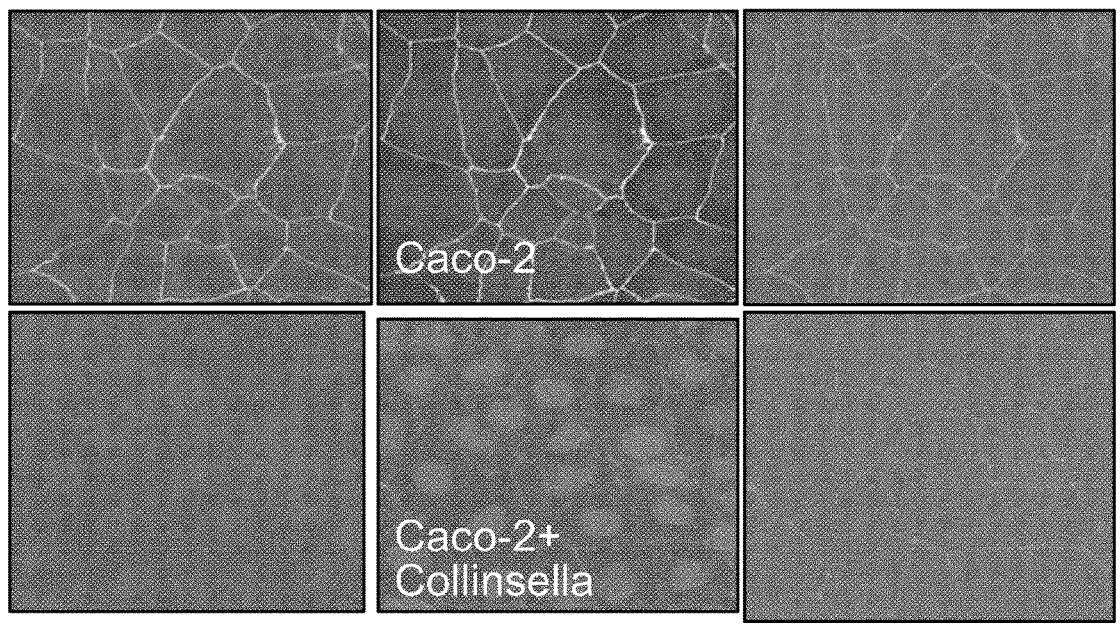
FIGS. 17A-D. *Collinsella* reduces the expression of the tight junction protein ZO-1. (A) CACO-2 cells cultured with or without *Collinsella* stained with ZO-1 and Occludin showed differences in the expression of tight junction proteins. (B) Quantification of the mean fluorescence intensity of ZO-1 and Occludin expression in CACO-2 cells cultured alone or in the presence of *Collinsella*, # P<0.05. *P<0.01. (C) Increased gut permeability was observed in DQ8 mice when *Collinsella* was administered. Sera of mice were tested for FITC-Dextran before and after treating mice with *Collinsella* for 3 weeks,*P<0.01. (D) Fold difference in the expression of Th17 regulatory cytokines/chemokines transcripts in CACO-2 cells cultured with *C. aerofaciens* as compared to CACO-2 cells cultured with bacterial growth media. Experiments were repeated for reproducibility.

*Collinsella* Increases Gut Permeability by Reducing the Expression of Tight Junction Protein in Epithelial Cells and Induces Expression of IL-17 Network Cytokines The mechanism by which *Collinsella* may contribute to RA pathogenesis in the gut was determined. Human intestinal epithelial cell line CACO-2 was cultured in the presence or absence of *Collinsella* or supernatants in which *Collinsella* was grown. The results suggest a decrease in the expression of tight junction protein Zo-1 in the presence of *Collinsella* and supernatant (FIG. 10D and FIG. 17A). Quantification of the mean fluorescence intensity revealed a significant difference between the healthy CACO-2 cells and those cultured with *Collinsella*. (FIG. 10E). These results demonstrate that *Collinsella* may be able to reduce epithelial integrity in the gut, thus causing leaky gut.

Figure 17B:
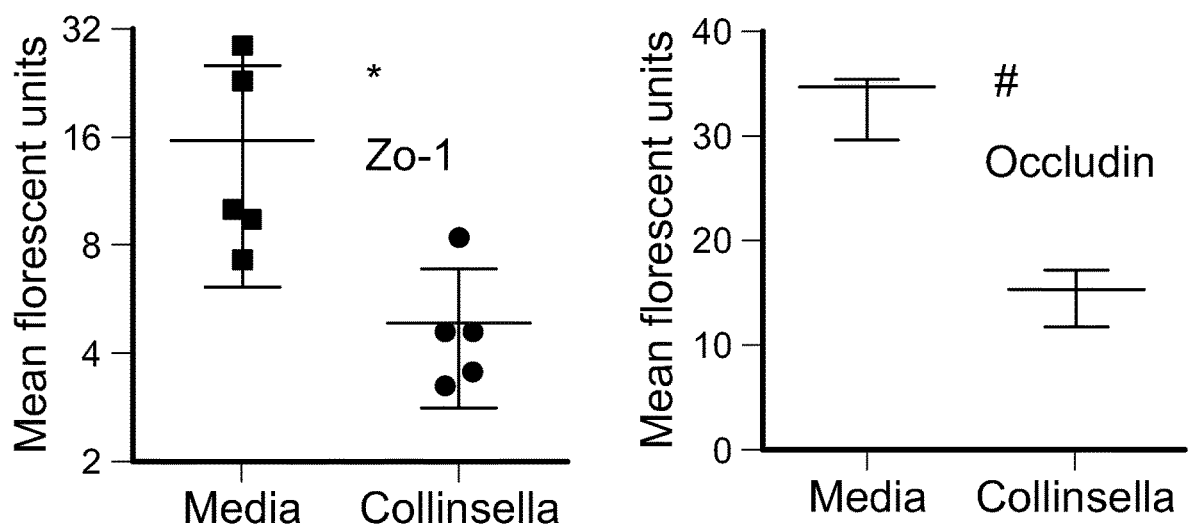
Figure 17C:
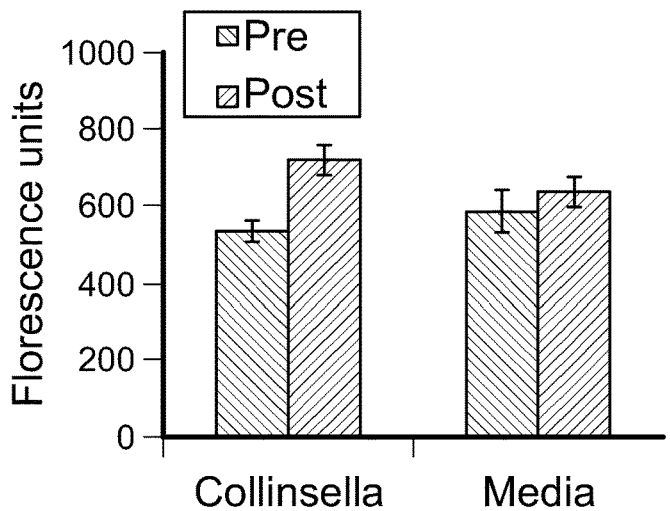
Figure 17D:
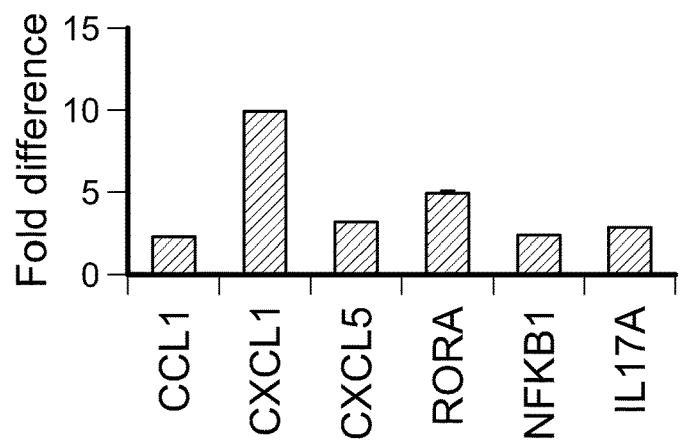
Figure 18:
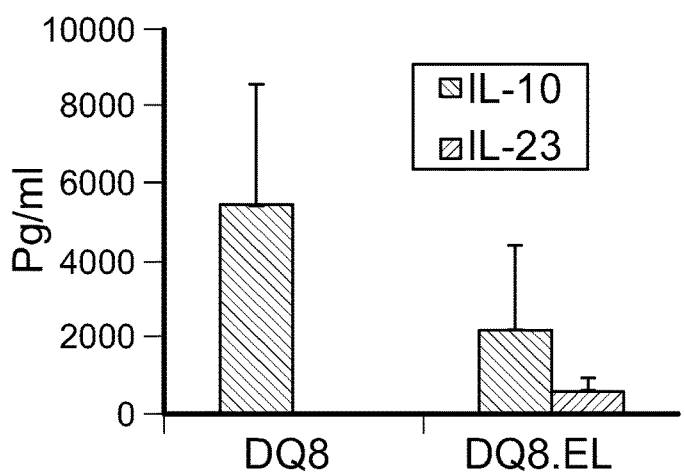
FIG. 18. Lymph node cells from DQ8.AE$^{-/-}$ mice (N=4) were transferred in DQ8.NOD SCID γc$^{-/-}$ mice. Mice were immunized with type II collagen. Two mice were gavaged with *Eggerthella lenta* (DQ8.EL) 4 weeks after immunization. 8 weeks later, levels of IL-10 and IL-23 were measured in sera of all mice. *Eggerthella lenta* gavaged mice produced lower levels of IL-10 than non-treated mice. Gavaging *E. lenta* led to production of IL-23 not observed in untreated mice suggesting *E. lenta* may be involved in production of proinflammatory cytokines.

To determine if *Collinsella* lowers gut permeability, gut permeability before and after administering media (N=3) or *Collinsella* (N=3) for 3 weeks was compared. *Collinsella* administration led to a significant increase in gut permeability as compared to pre-treatment, P<0.01. It also was determined if *Collinsella* induced expression of Th17 regulatory network cytokines in CACO-2 cells (FIG. 17B). Compared to controls, culturing with *Collinsella* led to more than a 2-fold increase in the expression of IL-17A as well as RORα and chemokines CXC11 and CXCL5, which are known to regulate production of IL-17 (Nouailles et al., *J. Clin. Invest.*, 124(3):1268-82 (2014); and Yang et al., *Immunity*, 28(1):29-39 (2008)) (FIGS. 17C and 17D). Also, an increase in NFkB1 expression suggested activation of inflammatory pathways. These data suggest that an expansion of *Collinsella* may cause an increase in pro-inflammatory conditions with a loss of gut epithelial integrity. In addition, *Eggerthella lenta* led to a reduction of IL-10 levels in treated mice (FIG. 17).

Taken together, the results provided herein suggest that susceptibility to RA could be triggered by the gut dysbiosis and pathways in which the rare lineages may be involved. The role of *Collinsella* in disease pathogenesis was confirmed in humanized mice. Collectively, these results demonstrate the existence of a dysbiotic gut microbiota in RA patients, which can be modulated by prebiotics or probiotics.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating arthritis, wherein said method comprises:
   (a) identifying a mammal as having arthritis,
   (b) administering an antibiotic to said mammal to reduce the number of microbial organisms within the gut of said mammal, and
   (c) administering a formulation comprising live *Prevotella*, *Faecalibacterium*, *Lachnobacterium*, or a combination thereof and no other type of microbial organism to said mammal.

2. The method of claim 1, wherein said step (c) is performed between 2 days and 5 days after said step (b).

* * * * *